United States Patent
Ziman et al.

(10) Patent No.: US 7,229,765 B2
(45) Date of Patent: Jun. 12, 2007

(54) **RANDOM-PRIMED REVERSE TRANSCRIPTASE-*IN VITRO* TRANSCRIPTION METHOD FOR RNA AMPLIFICATION**

(75) Inventors: Michael Ziman, San Francisco, CA (US); Colleen P. Davis, Seattle, WA (US)

(73) Assignee: Rosetta Inpharmatics LLC, Seattle, WA (US)

( * ) Notice: Subject to any disclaimer, the term of this patent is extended or adjusted under 35 U.S.C. 154(b) by 524 days.

(21) Appl. No.: 10/432,176

(22) PCT Filed: Nov. 28, 2001

(86) PCT No.: PCT/US01/44821

§ 371 (c)(1),
(2), (4) Date: Nov. 13, 2003

(87) PCT Pub. No.: WO02/44399

PCT Pub. Date: Jun. 6, 2002

(65) Prior Publication Data

US 2004/0081978 A1    Apr. 29, 2004

(51) Int. Cl.
*C12Q 1/68* (2006.01)
(52) U.S. Cl. ........................................ 435/6
(58) Field of Classification Search ............. 435/6
See application file for complete search history.

(56) References Cited

U.S. PATENT DOCUMENTS

| | | | |
|---|---|---|---|
| 5,554,516 A | 9/1996 | Kacian et al. | |
| 5,716,785 A | 2/1998 | Van Gelder et al. | |
| 5,932,451 A * | 8/1999 | Wang et al. | 435/91.21 |
| 6,132,997 A | 10/2000 | Shannon | |
| 6,235,483 B1 | 5/2001 | Wolber et al. | |
| 6,495,320 B1 * | 12/2002 | Lockhart et al. | 435/6 |

FOREIGN PATENT DOCUMENTS

| | | |
|---|---|---|
| WO | WO 01/09310 A1 | 2/2001 |
| WO | WO 01/71036 A2 | 9/2001 |

OTHER PUBLICATIONS

Ahern, H., "Biochemical, Reagent Kits Offer Scientists Good Return on Investment," *The Scientist* 9(15):20-24, 1995.

* cited by examiner

*Primary Examiner*—Kenneth R. Horlick
*Assistant Examiner*—Cynthia B. Wilder
(74) *Attorney, Agent, or Firm*—Christensen O'Connor Johnson Kindness PLLC

(57) ABSTRACT

A random-primed reverse transcriptase-in vitro transcription method of linearly amplifying RNA is provided. According to the methods of the invention, source RNA (or other single-stranded nucleic acid), preferably, mRNA, is converted to double-stranded cDNA using two random primers, one of which comprises a RNA polymerase promoter sequence ("promoter-primer"), to yield a double-stranded cDNA that comprises a RNA polymerase promoter that is recognized by a RNA polymerase. Preferably, the primer for first-strand cDNA synthesis is a promoter-primer and the primer for second-strand cDNA synthesis is not a promoter-primer. The double-stranded cDNA is then transcribed into RNA by the RNA polymerase, optimally in the presence of a reverse transcriptase that is rendered incapable of RNA-dependent DNA polymerase activity during this transcription step. The subject methods produce linearly amplified RNA with little or no 3' bias in the sequences of the nucleic acid population amplified.

21 Claims, 4 Drawing Sheets

Figure 1:
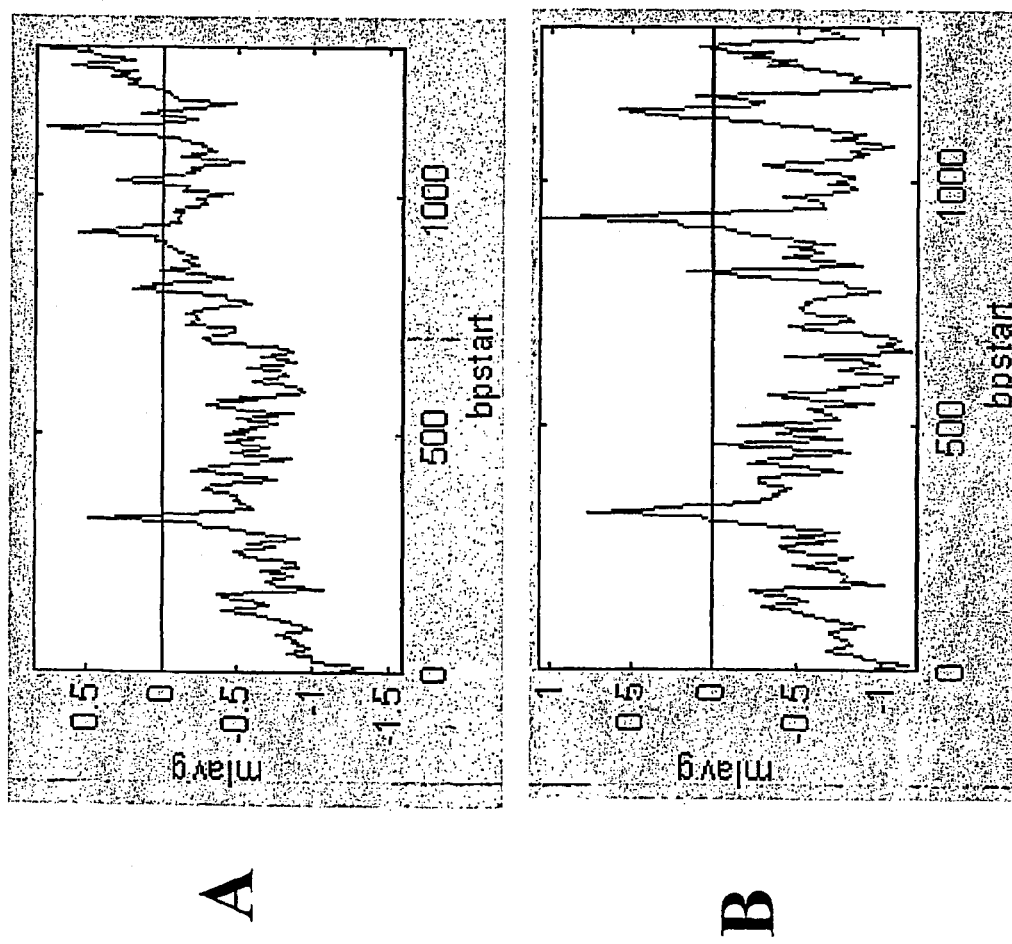

FIGS. 1(A-B) Single-gene analysis

FIGS. 3(A-C)
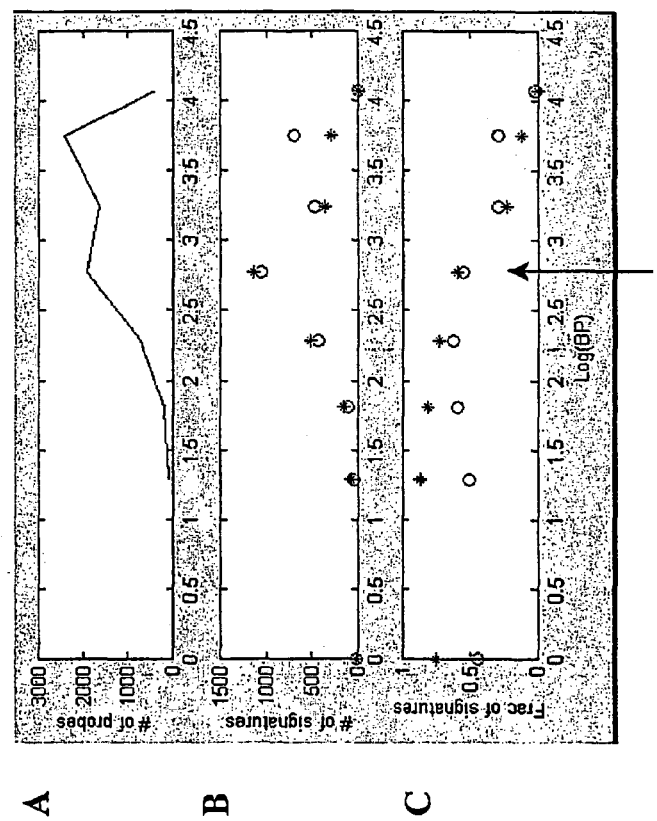

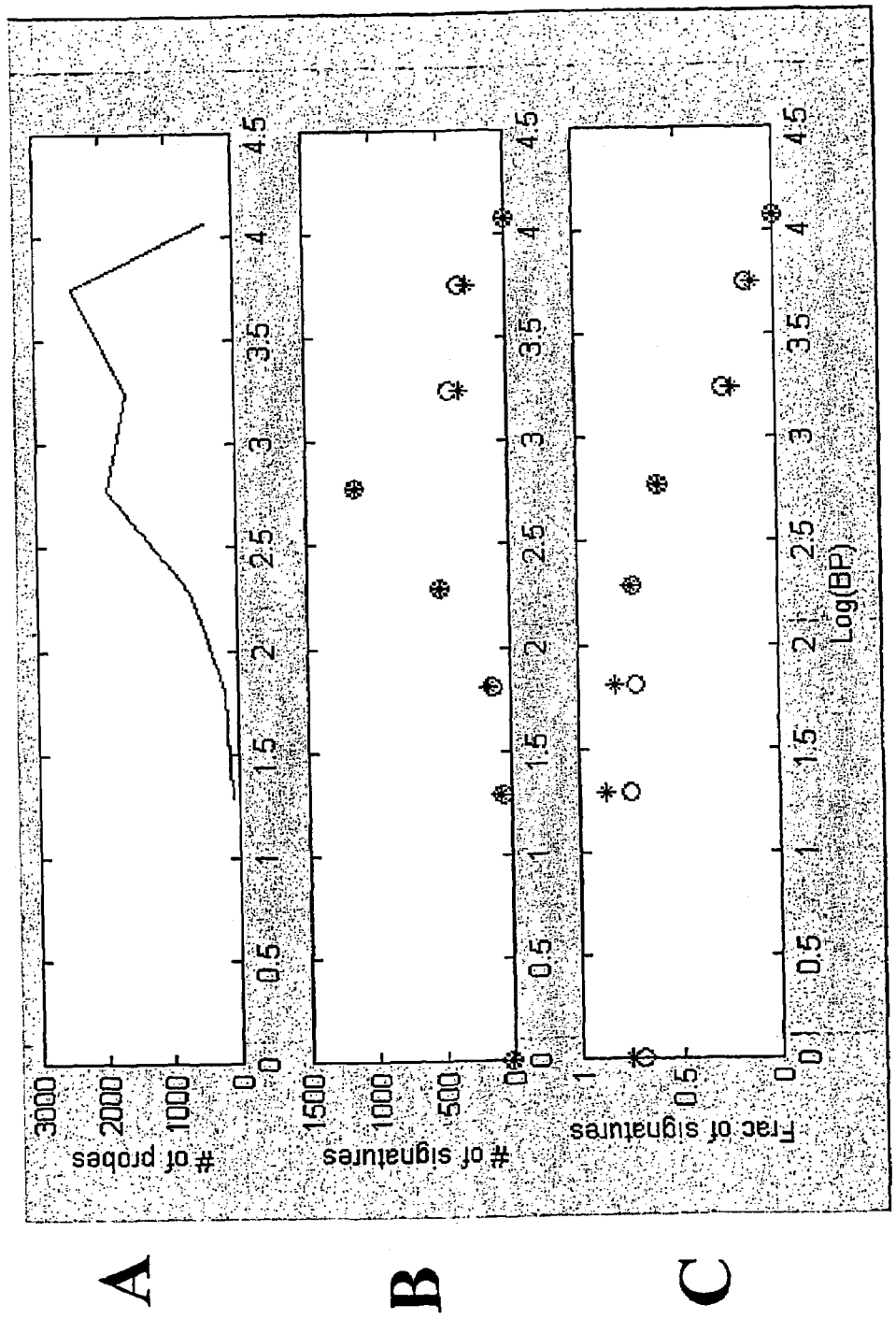
FIGS. 4(A-C)

RANDOM-PRIMED REVERSE TRANSCRIPTASE-*IN VITRO* TRANSCRIPTION METHOD FOR RNA AMPLIFICATION

1. TECHNICAL FIELD

The present invention relates to enzymatic amplification of nucleic acids using two random primers, one of which contains a RNA polymerase promoter sequence, to generate a double stranded DNA template, and in vitro transcription.

2. BACKGROUND OF THE INVENTION

The characterization of cellular gene expression finds application in a variety of disciplines, such as in the analysis of differential expression between different tissue types, different stages of cellular growth or between normal and diseased states. Recently, changes in gene expression have also been used to assess the activity of new drug candidates and to identify new targets for drug development. The latter objective is accomplished by correlating the expression of a gene or genes known to be affected by a particular drug with the expression profile of other genes of unknown function when exposed to that same drug; genes of unknown function that exhibit the same pattern of regulation, or signature, in response to the drug are likely to represent novel targets for pharmaceutical development. One particularly useful method of assaying gene expression at the level of transcription employs DNA microarrays (Ramsay, Nature Biotechnol. 16: 40–44, 1998; Marshall and Hodgson, Nature Biotechnol. 16: 27–31, 1998; Lashkari et al., Proc. Natl. Acad. Sci. (USA) 94: 130–157, 1997; DeRisi et al., Science 278: 680–6, 1997).

A number of methods for the amplification of nucleic acids have been described. Such methods include the "polymerase chain reaction" (PCR) (Mullis et al., U.S. Pat. No. 4,683,195), and a number of transcription-based amplification methods (Malek et al., U.S. Pat. No. 5,130,238; Kacian and Fultz, U.S. Pat. No. 5,399,491; Burg et al., U.S. Pat. No. 5,437,990). Each of these methods uses primer-dependent nucleic acid synthesis to generate a DNA or RNA product, which serves as a template for subsequent rounds of primer-dependent nucleic acid synthesis. Each process uses (at least) two primer sequences complementary to different strands of a desired nucleic acid sequence and results in an exponential increase in the number of copies of the target sequence. These amplification methods can provide enormous amplification (up to billion-fold). However, these methods have limitations that make them not amenable for gene expression monitoring applications. First, each process results in the specific amplification of only the sequences that are bounded by the primer binding sites. Second, exponential amplification can introduce significant changes in the relative amounts of specific target species—small differences in the yields of specific products (for example, due to differences in primer binding efficiencies or enzyme processivity) become amplified with every subsequent round of synthesis.

Amplification methods that utilize a primer containing a RNA polymerase promoter sequence ("promoter-primer") are amenable to the amplification of heterogeneous mRNA populations. The vast majority of mRNAs carry a homopolymer of 20–250 adenosine residues on their 3' ends (the poly-A tail), and the use of poly-dT primers for cDNA synthesis is a fundamental tool of molecular biology.

"Single-primer amplification" protocols have been reported (see e.g., Kacian et al., U.S. Pat. No. 5,554,516; Van Gelder et al., U.S. Pat. No. 5,716,785). The methods reported in these patents utilize a single promoter-primer containing a RNA polymerase promoter sequence and a sequence complementary to the 3'-end of the desired nucleic acid target sequence(s). In both methods, the promoter-primer is added under conditions in which it hybridizes to the target sequence(s) and is converted to a substrate for RNA polymerase. In both methods, the substrate intermediate is recognized by RNA polymerase, which produces multiple copies of RNA complementary to the target sequence(s) ("antisense RNA"). Each method uses, or could be adapted to use, a primer containing poly-dT for amplification of heterogeneous mRNA populations.

Amplification methods that proceed linearly during the course of the amplification reaction are less likely to introduce bias in the relative levels of different mRNAs than those that proceed exponentially. In the method described in Kacian et al., U.S. Pat. No. 5,554,516, the amplification reaction contains a nucleic acid target sequence, a promoter-primer, a RNA polymerase, a reverse transcriptase, and reagent and buffer conditions sufficient to allow amplification. The amplification proceeds in a single tube under conditions of constant temperature and ionic strength. Under these conditions, the antisense RNA products of the reaction can serve as substrates for further amplification by non-specific priming and extension by the RNA-dependent DNA polymerase activity of reverse transcriptase. As such, the amplification described in U.S. Pat. No. 5,554,516 proceeds exponentially. In contrast, in specific examples described in Van Gelder et al., U.S. Pat. No. 5,716,785, cDNA synthesis and transcription occur in separation reactions separated by phenol/chloroform extraction and ethanol precipitation (or dialysis), which may incidentally allow for the amplification to proceed linearly since the RNA products cannot serve as substrates for further amplification.

The method described in U.S. Pat. No. 5,716,785 has been used to amplify cellular mRNA for gene expression monitoring (for example, R. N. Van Gelder et al. (1990), Proc. Natl. Acad. Sci. USA 87, 1663; D. J. Lockhart et al. (1996), Nature Biotechnol. 14, 1675). However, this procedure is not readily amenable to high throughput processing. In preferred embodiments of the method described in U.S. Pat. No. 5,716,785, poly-A mRNA is primed with a promoter-primer containing poly-dT and converted into double-stranded cDNA using a method described by Gubler and Hoffman (U. Gubler and B. J. Hoffman (1983), Gene 25, 263–269) and popularized by commercially available kits for cDNA synthesis. Using this method for cDNA synthesis, first strand synthesis is performed using reverse transcriptase and second strand cDNA is synthesized using RNaseH and DNA polymerase I. After phenol/chloroform extraction and dialysis, double-stranded cDNA is transcribed by RNA polymerase to yield antisense RNA product. The phenol/chloroform extractions and buffer exchanges required in this procedure are labor intensive, and are not readily amenable to robotic handling.

A method of linear amplification of mRNA into antisense RNA has been recently developed, U.S. Pat. No. 6,132,997 issued to Shannon ("Shannon"), which is incorporated by reference in its entirety for all purposes. Shannon does not require a reverse transcriptase separation step and is therefore readily amenable to high throughput processing. Shannon discloses a method in which mRNA is converted to cDNA (particularly double-stranded cDNA) using a promoter-primer having a poly-dT primer site linked to a promoter sequence so that the resulting cDNA is recognized by a RNA polymerase. The resultant cDNA is then transcribed into RNA (particularly antisense RNA) in the presence of a reverse transcriptase that is rendered incapable of RNA-dependent DNA polymerase activity during the transcription step.

A significant drawback of the Shannon method, however, is that it produces a 3' bias in the amplification of mRNA. Sequences that are more than 1000 bp from the 3' end to which the primer has hybridized are underamplified with respect to sequences that are less than 1000 bp from the 3' end, i.e., the sequences that are more than 1000 bp from the 3' end are amplified in less than linear amounts.

Thus there exists a need in the art for an improved method of linear amplification of mRNA that is amenable to high throughput processing, that produces little or no 3' bias, that improves the ability to detect the 5' ends of mRNA, and therefore achieves good representation of both the 3' and 5' regions of an original mRNA in the amplified complementary RNA (cRNA).

3. SUMMARY OF THE INVENTION

A random-primed reverse transcriptase-in vitro transcription method of linearly amplifying RNA is provided. According to the methods of the invention, source RNA (or other single-stranded nucleic acid), preferably, mRNA, is converted to double-stranded cDNA using two random primers, one of which comprises a RNA polymerase promoter sequence ("promoter-primer"), to yield a double-stranded cDNA that comprises a RNA polymerase promoter that is recognized by a RNA polymerase. Preferably, the primer for first-strand cDNA synthesis is a promoter-primer and the primer for second-strand cDNA synthesis is not a promoter-primer. The double-stranded cDNA is then transcribed into RNA by the RNA polymerase, optimally in the presence of a reverse transcriptase that is rendered incapable of RNA-dependent DNA polymerase activity during this transcription step. The subject methods of producing linearly amplified RNA provide an improvement over prior methods in that little or no 3' bias in the sequences of the nucleic acid population amplified is produced, and the ability to detect the 5' end sequences of the nucleic acids is improved. The methods of the invention therefore achieve good representation of both the 3' and 5' regions of the source nucleic acid in the amplified complementary RNA (cRNA). Linear amplification extents of at least 100-fold can be achieved using the subject methods. All of the benefits of linear amplification are achieved with the subject methods, such as the production of unbiased antisense RNA libraries from heterogeneous mRNA mixtures.

In particular, the invention provides a method for linearly amplifying one or more single stranded nucleic acids, said method comprising (a) contacting said one or more single stranded nucleic acids with a first set of oligonucleotides, each of which comprises a promoter sequence and a sequence from a set of random sequences of at least 4 nucleotides (but preferably 6 to 9 nucleotides, more preferably 9 nucleotides), a second set of oligonucleotides, each of which comprises (preferably, consists of) of one or a set of random sequences of at least 4 nucleotides (but preferably 6 to 9 nucleotides, more preferably 6 nucleotides) and one or more enzymes that alone or in combination catalyze the synthesis of double-stranded cDNA, under conditions suitable for the production of double-stranded cDNA; and (b) contacting the double-stranded cDNA produced in step (a) with a RNA polymerase that recognizes said promoter sequence and ribonucleotides under conditions suitable to effect transcription, thereby producing sense or antisense RNA copies corresponding to said one or more single stranded nucleic acids. In a preferred embodiment, the second set of oligonucleotides does not contain a promoter sequence. Alternatively, the cDNA may be generated in two steps where the first step is the synthesis of first strand cDNA using the first set of oligonucleotides and one or more enzymes that catalyze first strand cDNA synthesis and the second step is the synthesis of double-stranded cDNA by contacting the first strand cDNA made in the first step with the second set of oligonucleotides and one or more enzymes that alone or in combination catalzye second strand cDNA synthesis. In preferred embodiments, the enzyme used in step (a) is a reverse transcriptase. In an alternative embodiment, the single-stranded nucleic acid is also contacted in step (a) with a promoter-primer containing the same promoter sequence used in the set of random primer-promoter primers used in step (a) and a polydT sequence of at least 4 nucleotides (preferably at least 5 nucleotides, more preferably 15 to 25 nucleotides, and most preferably 18 nucleotides).

The invention further provides kits for carrying out the linear amplification methods of the invention containing one or more components used in the methods of the inventions and instructions for use. In a particular embodiment, the invention provides a kit for use in linearly amplifying single stranded nucleic acids into sense or antisense RNA, said kit comprising a first set of oligonucleotides each comprising a promoter sequence and one of a set of random sequences of at least 4 nucleotides; and a second set of oligonucleotides each of which comprises (preferably, consists of) of one of a set of random sequences of at least four nucleotides. In a preferred embodiment the second set of oligonucleotides does not contain a promoter sequence In another embodiment, the kit also contains a reverse transcriptase and a RNA polymerase. In yet another embodiment, the kit further contains, in addition to the two sets of random primers, oligonucleotides containing the same promoter sequence as the random primer-promoter primer oligonucleotide and a polydT sequence of at least 5 nucleotides (preferably 18 nucleotides).

4. DESCRIPTION OF THE FIGURES.

FIGS. 1(A–B). Comparison of profiles obtained from single-gene analysis using (A) the mRNA amplification method described in U.S. Pat. No. 6,132,997 (Shannon, issued Oct. 17, 2000) ("Shannon") and (B) the random-primed reverse transcriptase-in vitro transcription (RT-IVT) method of the invention. The graphs plot signal intensity (mlavg) of oligonucleotides in a single gene (X-axis) as a function of the number of base pairs from the 5' end (Y-axis). The 3' bias of signal intensity seen when the Shannon method is used cannot be seen when the random-primed RT-IVT method is used, indicating that the random-primed RT-IVT method overcomes the 3' bias of the Shannon method.

Figure 2:
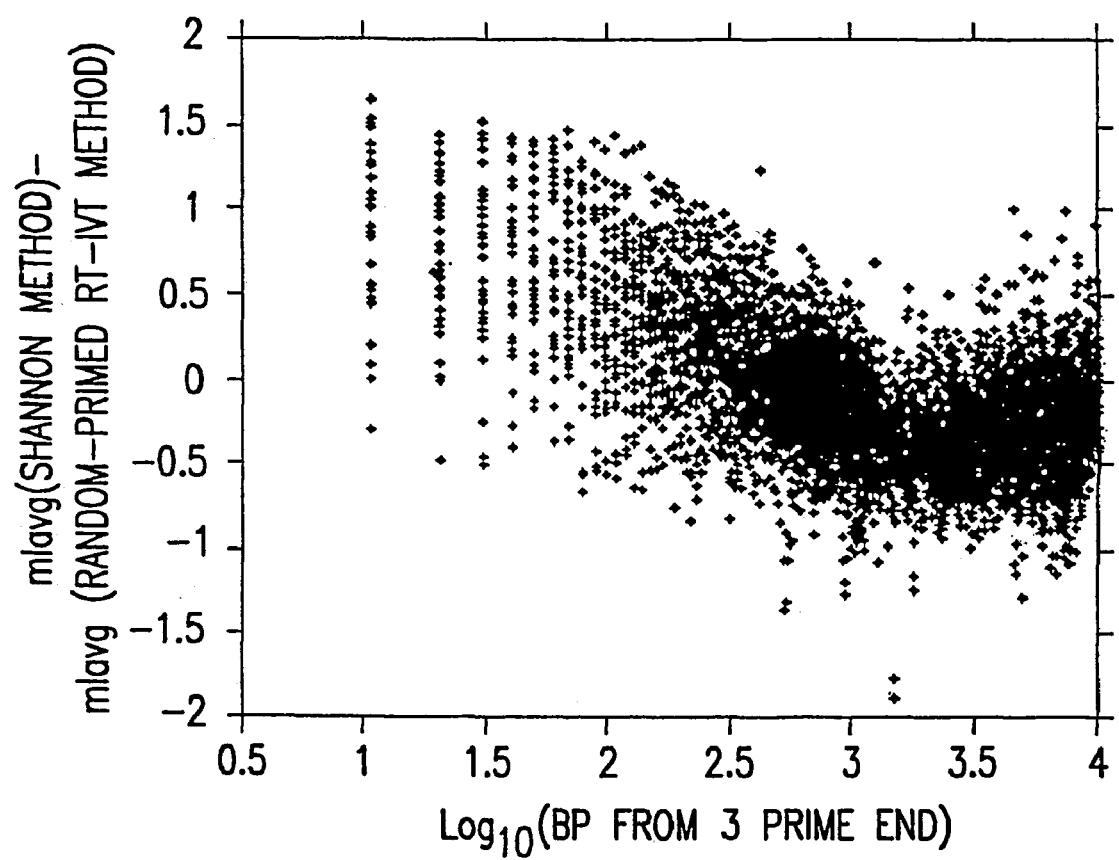

FIG. 2. Intensity difference as a function of distance from the 3' end. The graph shows the intensity of all oligonucleotides as a function of distance from the 3' end. The graph plots mlavg (Shannon method)–mlavg (random-primed RT-IVT method) (X-axis) versus $\log_{10}$ of the number of bp from the 3' end (Y-axis). The intensity obtained with the Shannon method is greater than the intensity obtained with the random-primed RT-IVT method for probes less than 1000 bp from the 3' end of the message. The intensity obtained with the Shannon method is less than the intensity obtained with the random-primed RT-IVT method for probes greater than 1000 bp from the 3' end of the message.

FIGS. 3(A–C). Signature differences in the numbers and percentages of significant data points. The top graph (A) plots the number of probes (X-axis) versus the $\log_{10}$ (bp) (Y-axis). The middle graph (B) plots the number of signatures (X-axis) versus the $\log_{10}$ (bp) (Y-axis). The bottom graph (C) plots the fraction of signatures versus the $\log_{10}$ (bp) (Y-axis). As can be seen in the bottom graph, the random-primed RT-IVT method outcompetes the Shannon method for probes greater than 1000 bp from the 3' end. Note the black arrow at approximately 700 bp where random-primed RT-IVT method is more representative than the Shannon method. Stars: Shannon method. Circles: random-primed RT-IVT method.

FIGS. 4(A–C). Shows the results obtained when the amplification methods of the invention were run using a primer comprising a T7 RNA polymerase promoter site and an poly-$dT_{18}$ sequence ("T7-$dT_{18}$"), in addition to using random T7-$dN_9$ and $dN_6$ primers. The top graph (A) plots the number of probes (X-axis) versus the $\log_{10}$ (bp) (Y-axis). The middle graph (B) plots the number of signatures (X-axis) versus the $\log_{10}$ (bp) (Y-axis). The bottom graph (C) plots the fraction ("frac") or percentage of signatures versus the $\log_{10}$ (bp) (Y-axis). As can be seen in the bottom graph, the number of probes at greater than 1000 base pairs is greater with the random-primed RT-IVT method. Using both the T7-$dT_{18}$ and random T7-$dN_9$ primers for first strand cDNA synthesis improves the fraction of statistically significant probes more efficiently than either the Shannon method or the method of the invention in which just the random T7-$dN_9$ primer is used. Stars: Shannon method. Circles: random-primed RT-IVT method.

5. DETAILED DESCRIPTION OF THE INVENTION

A random-primed reverse transcriptase-in vitro transcription (RT-IVT) method of linearly amplifying RNA is provided. According to the methods of the invention, source RNA (or other single-stranded nucleic acid), preferably, mRNA, is converted to double-stranded cDNA using two random primers, one of which comprises a RNA polymerase promoter sequence ("promoter-primer"), to yield a double-stranded cDNA that comprises a RNA polymerase promoter that is recognized by a RNA polymerase. Thus, "promoter sequence" refers to a single-stranded nucleotide sequence that when double-stranded (i.e., paired with its reverse-complement) forms a RNA polymerase promoter that is recognized by a RNA polymerase. Preferably, the primer for first-strand cDNA synthesis is a promoter-primer and the primer for second-strand cDNA synthesis is not a promoter-primer. Optionally, the cDNA synthesis reaction contains a mixture of the random-sequence-promoter primer and an oligonucleotide containing the promoter sequence and an oligodT sequence. The double-stranded cDNA is then transcribed into RNA by the RNA polymerase, optimally in the presence of a reverse transcriptase that is rendered incapable of RNA-dependent DNA polymerase activity during this transcription step.

The subject methods of producing linearly amplified RNA provide an improvement over prior methods in that little or no 3' bias in the sequences of the nucleic acid population amplified is produced, and the ability to detect the 5' end sequences of the nucleic acids is improved. The methods of the invention therefore achieve good representation of both the 3' and 5' regions of the source nucleic acid in the amplified complementary RNA (cRNA). Linear amplification extents of at least 100-fold can be achieved using the subject methods. All of the benefits of linear amplification are achieved with the subject methods, such as the production of unbiased antisense RNA libraries from heterogeneous mRNA mixtures.

For clarity of disclosure, and not by way of limitation, the detailed description of the invention is divided into the subsections set forth below.

5.1. Methods of Nucleic Acid Amplification

The invention provides methods for producing amplified amounts of either sense or antisense RNA from an initial amount of source single-stranded nucleic acid, preferably poly-$A^+$ RNA or mRNA. By amplified amounts is meant that for each initial source of nucleic acid, multiple corresponding sense or antisense RNAs are produced. The term antisense RNA is defined here as RNA complementary to the source single-stranded nucleic acid. By corresponding is meant that the sense or antisense RNA shares a substantial sequence identity with the sequence of, or the sequence complementary to (i.e., the complement of the initial source nucleic acid), the source nucleic acid. Substantial sequence identity means at least 95%, usually at least 98%, and more usually at least 99%, and, in certain embodiments, 100% sequence identity, where sequence identity is determined using the BLAST algorithm, as described in Altschul et al. (1990), J. Mol. Biol. 215:403–410 (using the published default setting, i.e., parameters w=4, t=17). Generally, the number of corresponding antisense RNA molecules produced for each initial nucleic acid during the subject linear amplification methods will be at least about 10, usually at least about 50, more usually at least about 100, and may be as great as 600 or greater, but often does not exceed about 1000.

The subject methods can be used to produce amplified amounts of RNA corresponding to substantially all of the nucleic acid present in the initial sample, or to a proportion or fraction of the total number of distinct nucleic acids present in the initial sample. By substantially all of the nucleic acid present in the sample is meant more than 90%, usually more than 95%, where that portion not amplified is solely the result of inefficiencies of the reaction and not intentionally excluded from amplification.

In a specific embodiment, only a single cycle of reverse transcription is carried out. In alternative embodiments, more than one cycle of reverse transcription is performed (with transcription and denaturation between cycles). For example, in a specific embodiment, a first cycle of reverse transcription is carried out wherein one or more single stranded nucleic acids are (a) contacted with a first set of oligonucleotides, each of which comprises a promoter sequence and a sequence from a set of random sequences of at least 4 nucleotides (but preferably 6 to 9 nucleotides, more preferably 9 nucleotides), a second set of oligonucleotides, each of which comprises (preferably, consists of) of one or a set of random sequences of at least 4 nucleotides (but preferably 6 to 9 nucleotides, more preferably 6 nucleotides) and one or more enzymes that alone or in combination catalyze the synthesis of double-stranded cDNA, under conditions suitable for the production of double-stranded cDNA. The resultant double-stranded cDNA is then (b) contacted with a RNA polymerase that recognizes said promoter sequence and ribonucleotides under conditions suitable to effect transcription (i.e., in vitro transcription or "IVT"), thereby producing sense or antisense RNA copies corresponding to said one or more single stranded nucleic acids. The resultant sense or antisense RNA copies are then reverse transcribed in a second cycle of reverse transcription, as described in step (a) above, and the resultant double-stranded cDNA is then transcribed via IVT into sense or antisense RNA copies as described in step (b) above. Additional cycles of RT-IVT may be performed to obtain the desired quantity of sense or antisense RNA copies.

According to the methods of the invention, additional linear amplification is afforded by a subsequent in vitro transcription (IVT) step as described below in Section 5.2. During IVT, the double-stranded cDNA produced in the first step is transcribed by RNA polymerase to yield RNA that is complementary to the initial RNA target from which it is amplified. This combination of cDNA synthesis and IVT enables the generation of a relatively large amount of cRNA from a very small starting amount of nucleic acid without loss of fidelity, and particularly, without 3' amplification bias.

In one embodiment of the invention (see Example 1, Section 6), 0.2 µg (200 ng) of source mRNA is used.

In another embodiment of the invention, nucleic acid amplification is performed in situ, on samples of preserved or fresh cells or tissues (see, e.g., Nuovo, 1997, *PCR In Situ Hybridization: Protocols and Applications, Third Edition*, Lippincott-Raven Press, New York).

The subject methods may be applied to other amplification systems in which an oligonucleotide is incorporated into an amplification product such as polymerase chain reaction (PCR) systems (U.S. Pat. No. 4,683,195, Mullis et al., entitled "Process for amplifying, detecting, and/or-cloning nucleic acid sequences," issued Jul. 28, 1987; U.S. Pat. No. 4,683,202, Mullis, entitled "Process for amplifying nucleic acid sequences," issued Jul. 28, 1987)

5.1.1. cDNA Synthesis

Double-stranded cDNA molecules can be synthesized from a collection of RNAs (or other single-stranded nucleic acids), e.g., mRNAs present in a population of cells, by methods well-known in the art. In order for the cDNAs produced in this step to be useful in the methods of the invention, it is necessary to incorporate a RNA polymerase promoter into the cDNA molecules during synthesis. This enables the cDNA molecules to serve as templates for RNA transcription. This is accomplished by choosing one or more primers for the cDNA synthesis reaction that comprise a single-stranded, synthetic oligonucleotide containing a RNA polymerase promoter sequence in sense orientation. This "promoter-primer" may be used to prime either first strand and/or second strand cDNA synthesis. In preferred embodiments, the "promoter-primer" primes first strand cDNA synthesis and the promoter is in the appropriate orientation to promote synthesis of antisense RNA.

Typically, only one RNA polymerase promoter sequence-containing primer is used during cDNA synthesis. Preferably, the promoter-primer is used to prime first strand cDNA synthesis. Following reverse transcription, the resultant RNA polymerase promoter-containing double-stranded cDNA is transcribed into RNA using a RNA polymerase capable of binding to the RNA polymerase promoter introduced during cDNA synthesis (see below Section 5.2).

In a preferred embodiment, the primer for first strand cDNA synthesis is a mixture of random primers linked to a promoter sequence that prime synthesis in a direction toward the 5' end of the nucleic acids (e.g., mRNAs) in the sample, and the primer for second strand cDNA synthesis is a mixture of random primers that prime synthesis of double-stranded cDNA from substantially all the first strand cDNAs thus produced.

Preferably, the first-strand primer is a random promoter-primer, wherein the random (poly-dN) sequence is operably linked to a RNA polymerase promoter sequence. In one aspect, the first-strand primer is a mixture of primers, each primer comprising a RNA polymerase promoter sequence and a 3' end or 3' distal sequence of 6–9 nucleotides, preferably 9 nucleotides. The mixture of primers comprises random primers, i.e., primers having an A, a G, a C, or a T residue present in each position of the 3' end sequence or 3' distal sequence (i.e., the non-promoter sequence). In particular, the random primer for priming first strand cDNA synthesis is a random promoter-primer that includes: (a) a poly-dN region for hybridization to the mRNA; and (b) a RNA polymerase promoter region 5' of the poly-dN region that is in an orientation capable of directing transcription of antisense RNA when it primes first strand cDNA synthesis. The poly-dN region is sufficiently long to provide for efficient hybridization to the mRNA, where the region typically ranges in length from 4–50 nucleotides in length, preferably 6–25 nucleotides in length, more preferably from 6–12, and most preferably, 9 nucleotides in length, i.e., a random 9-mer. In specific embodiments, the poly-dN region is 4, 5, 6, 7, 8, 9, 10, 11, or 12 nucleotides in length.

In a preferred embodiment, the random promoter-primer used to prime first strand cDNA synthesis is a random 9-mer operably linked to a T7 RNA polymerase promoter sequence (T7-dN$_9$: (5') AAT TAA TAC GAC TCA CTA TAG GGA GAT NNN NNN NNN (3') (N=A, T, C or G) (SEQ ID NO.: 1)).

In another embodiment, the random promoter-primers used to prime first strand cDNA synthesis are a complete set of all (or almost all) combinations of random 9-mers, i.e., a total of $4^9$ 9-mers, linked to a T7 RNA polymerase promoter sequence.

In another embodiment, a poly-dT primer comprising a RNA polymerase promoter sequence and a random dN primer comprising a RNA polymerase promoter sequence are used together to prime first strand cDNA synthesis. Preferably, the poly-dT-promoter primer and the random primer-promoter primer contain the same promoter sequence. In particular embodiments the poly-dT sequence is at least 5 thymidilate residues, preferably 15 to 25 residues and, preferably 18 residues. In a preferred embodiment, a T7-dT$_{18}$ primer and a T7-dN$_9$ primer are used to prime first strand cDNA synthesis.

A number of RNA polymerase promoters may be used for the promoter region of the promoter-primer. Suitable promoter regions will be capable of initiating transcription from an operably linked DNA sequence in the presence of ribonucleotides and a RNA polymerase under suitable conditions. The term "operably linked" refers to a functional linkage, i.e., the promoter will be linked in an orientation to permit transcription of sense or antisense RNA. Preferably the linkage is covalent, most preferably by a nucleotide bond. Most preferably, the promoter is linked in an orientation to permit transcription of antisense RNA when the promoter is incorporated into the first strand of cDNA synthesis. A linker oligonucleotide between the promoter and the DNA may be present, and if, present, will typically comprise between about 5 and 20 bases, but may be smaller or larger as desired. The promoter region is of sufficient length to promote transcription, and will usually comprise between about 15 and 250 nucleotides, preferably between about 17 and 60 nucleotides, from a naturally occurring RNA polymerase promoter or a consensus promoter region, as described in Alberts et al. (1989) in Molecular Biology of the Cell, 2d Ed. (Garland Publishing, Inc.), or any other variant that promotes transcription. In a specific embodiment, the promoter region is 36 nucleotides. Preferred promoter regions include the bacteriophage SP6 and T3 promoters and, most preferably, T7 promoters.

The random promoter-primer and/or the random primer may additionally contain a restriction site, in the middle or at the 5' distal end of the primer, but preferably not immediately at the 5' terminus. The restriction site may be used for cloning in to a vector. Restriction enzymes and the sites they recognize can be found, for example, in Sambrook et al., 1989, *Molecular Cloning—A Laboratory Manual* (2nd Ed.), Vol. 1, Chapter 5, Cold Spring Harbor Laboratory, Cold Spring Harbor, N.Y.

The primers of the invention may be prepared using any suitable method known in the art, e.g., as described in Section 5.3 infra.

Preferably both first- and second-strand cDNA synthesis is produced by reverse transcription, wherein DNA is made from RNA using the enzyme reverse transcriptase. Reverse transcriptase is found in all retroviruses and is commonly obtained from avian myeloblastoma virus or Moloney murine leukemia virus; enzyme from these sources is commercially available from Life Technologies (Gaithersburg, Md.) and Boehringer Mannheim (Indianapolis, Ind.).

The catalytic activities required to convert the promoter-primer-mRNA hybrid to double-stranded cDNA are a RNA-dependent DNA polymerase activity, a RNaseH activity, and a DNA-dependent DNA polymerase activity. Most reverse transcriptases, including those derived from Moloney murine leukemia virus (MMLV-RT), avian myeloblastosis virus (AMV-RT), bovine leukemia virus (BLV-RT), Rous sarcoma virus (RSV) and human immunodeficiency virus (HIV-RT) catalyze each of these activities. These reverse transcriptases are sufficient to convert a primer-mRNA hybrid to double-stranded DNA in the presence of additional reagents that include, but are not limited to: dNTPs; monovalent and divalent cations, e.g., KCl, $MgCl_2$; sulfhydryl reagents, e.g., dithiothreitol; and buffering agents, e.g., Tris-Cl. Alternatively, a variety of proteins that catalyze one or two of these activities can be added to the cDNA synthesis reaction. For example, MMLV reverse transcriptase lacking RNaseH activity (described in U.S. Pat. No. 5,405,776) catalyzes RNA-dependent DNA polymerase activity and DNA-dependent DNA polymerase activity. These proteins may be added together during a single reaction step, or added sequentially during two or more substeps. Preferably, MMLV is used for both first- and second-strand cDNA synthesis. As described above, preferably the reverse transcriptase is inactivated prior to or inhibited during the transcription step of the method.

In general, it is preferable for the RNA-containing sample to contain purified poly-$A^+$ RNA (mRNA). In one embodiment, a random promoter-primer is hybridized with an initial mRNA (poly-$A^+$ RNA) sample. The promoter-primer is contacted with the mRNA under conditions that allow the poly-dN site to hybridize to the mRNA. The random promoter-primer-mRNA hybrid is then converted to a double-stranded cDNA product that is recognized by a RNA polymerase.

In a preferred embodiment, first-strand cDNA synthesis is allowed to proceed at a lower temperature (for example, 25° C.) for a certain period of time (e.g., 10 min) prior to increasing the temperature (e.g., to 40° C.) for the remainder of the reverse transcription reaction, which improves annealing of the first primer (e.g., the promoter-primer) to its target nucleic acid sequence.

In the subject methods, conversion of the primer-mRNA hybrid to double-stranded cDNA proceeds by priming second strand cDNA synthesis with a random primer in the presence of a DNA-dependent DNA polymerase activity.

In another embodiment, the primer for second strand cDNA synthesis is a mixture of primers consisting of a poly-dN sequence that is sufficiently long to provide for efficient hybridization to the mRNA. The sequence typically ranges in length from 4–50, preferably 6–25, more preferably 6–12 or 6–9 and most preferably 6 degenerate bases, i.e., a random hexamer ($dN_6$), wherein the degenerate bases may be A, T, G, or C. (In theory, the primer should hybridize on average $4^6$ or 4096 base pairs from the 3' priming site of the first-strand cDNA.) In specific embodiments, the poly-dN sequence is 4, 5, 6, 7, 8, 9, 10, 11, or 12 nucleotides in length.

In a specific embodiment, the random primers used to prime second strand cDNA synthesis will be a complete set of all combinations of random hexamers, i.e., a total of $4^6$ or 4096 hexamers.

Additional proteins that may enhance the yield of double-stranded DNA products may also be added to the cDNA synthesis reaction. These proteins include a variety of DNA polymerases (such as those derived from *E. coli*, thermophilic bacteria, archaebacteria, phage, yeasts, Neurosporas, Drosophilas, primates and rodents), and DNA ligases (such as those derived from phage or cellular sources, including T4 DNA ligase and *E. coli* DNA ligase).

The second strand cDNA synthesis results in the creation of a double-stranded promoter region. The second strand cDNA includes not only a sequence of nucleotide residues that comprise a DNA copy of the mRNA template, but also additional sequences at its 3' end that are complementary to the promoter-primer used to prime first strand cDNA synthesis. The double-stranded promoter region serves as a recognition site and transcription initiation site for RNA polymerase, which uses the second strand cDNA as a template for multiple rounds of RNA synthesis during the next stage of the subject methods (see Section 5.2, "Transcription of cDNA," below).

Depending on the particular protocol, the same or different DNA polymerases may be employed during the cDNA synthesis step. In a preferred embodiment, a single reverse transcriptase, most preferably MMLV-RT, is used as a source of all the requisite activities necessary to convert the primer-mRNA hybrid to double-stranded cDNA. In another preferred embodiment, the polymerase employed in first strand cDNA synthesis is different from that which is employed in second strand cDNA synthesis. Specifically, a reverse transcriptase lacking RNaseH activity (e.g., SUPERSCRIPT II™) is combined with the primer-mRNA hybrid during a first substep for first strand synthesis. A source of RNaseH activity, such as *E. coli* RNaseH or MMLV-RT, but most preferably MMLV-RT, is added during a second substep to initiate second strand synthesis.

In yet other embodiments, the requisite-activities are provided by a plurality of distinct enzymes. The manner in which double-stranded cDNA is produced from the initial mRNA is not critical to certain embodiments of the invention. However, the preferred embodiments use MMLV-RT, or a combination of SUPERSCRIPT II™ and MMLV-RT, or a combination of SUPERSCRIPT II™ and *E. coli* RNaseH, for cDNA synthesis as these embodiments yield certain desired results. Specifically, in the preferred embodiments, reaction conditions were chosen so that enzymes present during the cDNA synthesis do not adversely affect the subsequent transcription reaction. Potential inhibitors include, but are not limited to, RNase contaminants of certain enzyme preparations.

5.2. Transcription of cDNA

The next step of the subject method is the preparation of RNA from the double-stranded cDNA prepared in the first step. During this step, the double-stranded cDNA produced in the first step is transcribed by RNA polymerase to yield RNA that, in certain embodiments, is complementary to the initial nucleic acid target from which it is amplified. This step is sometimes referred to as "in vitro transcription" (IVT).

The promoter regions that find use in the methods of the invention are regions where RNA polymerase binds tightly to the DNA and contain the start site and signal for RNA synthesis to begin. A wide variety of promoters are known and many are very well characterized. In general, prokaryotic promoters are preferred over eukaryotic promoters, and phage or virus promoters most preferred. The RNA polymerase promoter sequence is therefore preferably derived from a prokaryote such as E. coli or the bacteriophage T7, SP6, and T3, with the T7 RNA polymerase promoter sequence particularly preferred. T7, T3 and SP6 promoter regions are described in Chamberlin and Ryan, The Enzymes (ed. P. Boyer, Academic Press, New York) (1982) pp 87–108, which excerpt is hereby incorporated by reference in its entirety.

The RNA polymerase used for transcription must be capable of binding to the particular RNA polymerase promoter sequence contained in the primer; hence usually the RNA polymerase promoter sequence and the polymerase will be homologous. For example, if the T7 RNA polymerase promoter sequence is employed in the primer, it is preferred to use T7 RNA polymerase to drive transcription. T7 polymerase is commercially available from several sources, including Promega Biotech (Madison, Wis.) and Epicenter Technologies (Madison, Wis.).

In a preferred embodiment, the random promoter-primer used to prime first strand cDNA synthesis comprises a T7 promoter sequence-dN$_9$, and the RNA polymerase employed is T7 RNA polymerase.

Preferably, the RNA polymerase promoter sequence is located at or near the 5' terminus of the primer, in an orientation permitting transcription of the RNA population under study.

For this transcription step, the presence of the RNA polymerase promoter region on the double-stranded cDNA is exploited for the production of sense and/or antisense RNA. To synthesize the RNA, the double-stranded DNA is contacted with the appropriate RNA polymerase in the presence of the four ribonucleotides, under conditions sufficient for RNA transcription to occur.

In one embodiment, the conditions for RNA transcription are those described in Section 6, Example 1. Briefly, the transcription mix and the transcription reaction are as follows. 60 µl of Transcription Mix are aliquoted into each sample tube. The transcription reactions are incubated at 40° C. for 16 hrs.

| Transcription Mix | |
|---|---|
| Component | Volume (µl) |
| Nuclease-free water | 22.8 |
| 5x Transcription Buffer | 16 |
| 100 mM DTT | 6.0 |
| NTPs (25 mM A, G, C, 6.0 mM UTP) | 8.0 |
| aa UTP (allylamine-derivatized UTP) (75 mM) | 2.0 |
| 200 mM MgCl$_2$ | 3.3 |
| RNAGuard ™, Pharmacia (36 U/µl) | 0.5 |
| Inorganic Pyrophosphatase (200 U/ml) | 0.6 |
| T7 RNA polymerase (2500 U/µl) | 0.8 |
| Volume of Transcription Mix | 60 |

| Composition of Transcription Reaction | |
|---|---|
| Component | Final concentration or amount |
| Double-strand cDNA | Approximately 400 ng |
| Tris-HCl, pH 7.5 | 52 mM |
| MgCl$_2$ | 15 mM |
| KCl | 19 mM |
| NaCl | 10 mM |
| Spermidine | 2 mM |
| DTT | 10 mM |
| ATP, GTP, CTP | 2.5 mM each |
| UTP | 0.6 mM |
| aa UTP | 1.9 mM |
| T7 RNA polymerase | 2000 U |
| RNAGuard ™, Pharmacia | 18 U |
| Inorganic pyrophosphatase | 0.12 U |
| Total reaction volume | 80 µl |

Other suitable conditions for RNA transcription using RNA polymerases are known in the art, see e.g., Milligan and Uhlenbeck (1989), Methods in Enzymol. 180, 51 (which is hereby incorporated by reference in its entirety).

In one aspect of the invention, the transcription step is carried out in the presence of reverse transcriptase that is present in the reaction mixture from the double-stranded cDNA synthesis. Thus, the subject methods do not involve a step in which the double-stranded cDNA is physically separated from the reverse transcriptase following double-stranded cDNA preparation facilitating high throughput amplification and analysis. In this aspect of the invention, the reverse transcriptase that is present during the transcription step is rendered inactive. Thus, the transcription step is carried out in the presence of a reverse transcriptase that is unable to catalyze RNA-dependent DNA polymerase activity, at least for the duration of the transcription step. As a result, the RNA products of the transcription reaction cannot serve as substrates for additional rounds of cDNA synthesis, and the amplification process cannot proceed exponentially.

The reverse transcriptase present during the transcription step may be rendered inactive using any convenient protocol. The transcriptase may be irreversibly or reversibly rendered inactive. Where the transcriptase is reversibly rendered inactive, the transcriptase is physically or chemically altered so as to no longer be able to catalyze RNA-dependent DNA polymerase activity. The transcriptase may be irreversibly inactivated by any convenient means. Thus, the reverse transcriptase may be heat inactivated, in which the reaction mixture is subjected to heating to a temperature sufficient to inactivate the reverse transcriptase prior to commencement of the transcription step. In these embodiments, the temperature of the reaction mixture and therefore the reverse transcriptase present therein is typically raised to 55° C. to 70° C. for 5 to 60 minutes, usually to about 65° C. for 15 to 20 minutes.

Alternatively, reverse transcriptase may be irreversibly inactivated by introducing a reagent into the reaction mixture that chemically alters the enzyme so that it no longer has RNA-dependent DNA polymerase activity. In yet other embodiments, the reverse transcriptase is reversibly inactivated. In these embodiments, the transcription step may be carried out in the presence of an inhibitor of RNA-dependent DNA polymerase activity. Any convenient reverse transcriptase inhibitor may be employed that is capable of inhibiting RNA-dependent DNA polymerase activity a sufficient amount to provide for linear amplification. However, these inhibitors should not adversely affect RNA polymerase activity. Reverse transcriptase inhibitors of interest include ddNTPs, such as ddATP, ddCTP, ddGTP or ddTTP, or a combination thereof, the total concentration of the inhibitor typically ranges from about 50 µM to 200 µM.

Because of the nature of the subject methods, all of the necessary polymerization reactions, i.e., first strand cDNA synthesis, second strand cDNA synthesis and RNA transcription, may be carried out in the same reaction vessel at the same temperature, such that temperature cycling is not required. As such, the subject methods are particularly suited for automation, as the requisite reagents for each of the above steps need merely be added to the reaction mixture in the reaction vessel, without any complicated separation steps being performed, such as phenol/chloroform extraction. A further feature of the subject invention is that, despite its simplicity, it yields high amplification extents, where the amplification extents (mass of RNA product/mass of nucleic acid target) typically are at least about 50-fold, usually at least about 200-fold and may be as high as 600-fold or higher. Furthermore, such amplification extents are achieved with low variability, e.g., coefficients of variation about the mean amplification extents that do not exceed about 10%, and usually do not exceed about 5%.

The resultant cRNA (particularly antisense RNA) produced by the subject methods finds use in a variety of applications. RNA amplified by the methods of the invention may be labeled and employed to profile gene expression in different populations of cells. In a preferred embodiment, the amplified RNA is used for quantitative comparisons of gene expression between different populations of cells or between populations of cells exposed to different stimuli. For example, the resultant antisense RNA can be used in expression profiling analysis on such platforms as DNA microarrays, for construction of "driver" for subtractive hybridization assays, for cDNA library construction, and the like. Especially facilitated by the subject methods are studies of differential gene expression in mammalian cells or cell populations. The cells may be from blood (e.g., white cells, such as T or B cells) or from tissue derived from solid organs, such as brain, spleen, bone, heart, vascular, lung, kidney, liver, pituitary, endocrine glands, lymph node, dispersed primary cells, tumor cells, or the like.

The RNA amplification technology can also be applied to improve methods of detecting and isolating nucleic acid sequences that vary in abundance among different populations using the technique known as subtractive hybridization. In such assays, two nucleic acid populations, one sense and the other antisense, are allowed to mix with one another with one population being present in molar excess ("driver"). Under appropriate conditions, the sequences represented in both populations form hybrids, whereas sequences present in only one population remain single-stranded. Thereafter, various well known techniques are used to separate the unhybridized molecules representing differentially expressed sequences. The amplification technology described herein may be used to construct large amounts of antisense RNA for use as "driver" in such experiments.

5.3. Oligonucleotides

A primer may be prepared by any suitable method, such as phosphotriester and phosphodiester methods of synthesis, or automated embodiments thereof. It is also possible to use a primer that has been isolated from a biological source, such as a restriction endonuclease digest, although a synthetic primer is preferred.

An oligonucleotide primer can be DNA, RNA, chimeric mixtures or derivatives or modified versions thereof, so long as it is still capable of priming the desired reaction. The oligonucleotide primer can be modified at the base moiety, sugar moiety, or phosphate backbone, and may include other appending groups or labels, so long as it is still capable of priming the desired amplification reaction.

For example, an oligonucleotide primer may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid(v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid(v), 5-methyl-2-thiouracil, 3-(3-amino-3-N-2-carboxypropyl)uracil, (acp3)w, and 2,6-diaminopurine.

In another embodiment, the oligonucleotide primer comprises at least one modified sugar moiety selected from the group including but not limited to arabinose, 2-fluoroarabinose, xylulose, and hexose.

In yet another embodiment, the oligonucleotide primer comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

An oligonucleotide primer for use in the methods of the invention may be derived by cleavage of a larger nucleic acid fragment using non-specific nucleic acid cleaving chemicals or enzymes or site-specific restriction endonucleases; or by synthesis by standard methods known in the art, e.g., by use of an automated DNA synthesizer (such as are commercially available from Biosearch, Applied Biosystems, etc.) and standard phosphoramidite chemistry. As examples, phosphorothioate oligonucleotides may be synthesized by the method of Stein et al. (1988, Nucl. Acids Res. 16:3209–3221), methylphosphonate oligonucleotides can be prepared by use of controlled pore glass polymer supports (Sarin et al., 1988, Proc. Natl. Acad. Sci. U.S.A. 85:7448–7451), etc.

Once the desired oligonucleotide is synthesized, it is cleaved from the solid support on which it was synthesized and treated, by methods known in the art, to remove any protecting groups present. The oligonucleotide may then be purified by any method known in the art, including extraction and gel purification. The concentration and purity of the oligonucleotide may be determined by examining oligonucleotide that has been separated on an acrylamide gel, or by measuring the optical density at 260 nm in a spectrophotometer.

5.4. Methods of Labeling of Nucleic Acid Amplification Products

Nucleic acid amplification products such as amplified RNA may be labeled with any art-known detectable marker, including radioactive labels such as $^{32}P$, $^{35}S$, $^{3}H$, and the like; fluorophores; chemiluminescers; or enzymatic markers. In a preferred embodiment, the label is fluorescent. Exemplary suitable fluorophore moieties that can be selected as labels are listed in Table 1.

TABLE 1

Suitable fluorophore moieties that can be selected as labels 4-acetamido-4'-isothiocyanatostilbene-2,2'disulfonic acid
acridine and derivatives:
    acridine
    acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate (Lucifer Yellow VS)-(4-anilino-1-naphthyl)maleimide
anthranilamide
Brilliant Yellow
coumarin and derivatives:
    coumarin
    7-amino-4-methylcoumarin (AMC, Coumarin 120)
    7-amino-4-trifluoromethylcoumarin (Coumarin 151)
Cy3
Cy5
cyanosine
4',6-diaminidino-2-phenylindole (DAPI)
5',5''-dibromopyrogallol-sulfonephthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylarnino]naphthalene-1-sulfonyl chloride (DNS, dansyl chloride)
4-(4'-dimethylaminophenylazo)benzoic acid (DABCYL)
4-dimethylaminophenylazophenyl-4'-isothiocyanate (DABITC)
eosin and derivatives:
    eosin
    eosin isothiocyanate
erythrosin and derivatives:
    erythrosin B
    erythrosin isothiocyanate
ethidium
fluorescein and derivatives:
    5-carboxyfluorescein (FAM)
    5-(4,6-dichlorotriazin-2-yl)aminofluorescein (DTAF)
    2'7'-dimethoxy-4'5'-dichloro-6-carboxyfluorescein (JOE)
    fluorescein
    fluorescein isothiocyanate
    QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:

TABLE 1-continued

Suitable fluorophore moieties that can be selected as labels pyrene
    pyrene butyrate
    succinimidyl 1-pyrene butyrate
Reactive Red 4 (Cibacron ® Brilliant Red 3B-A)
rhodamine and derivatives:
    6-carboxy-X-rhodamine (ROX)
    6-carboxyrhodamine (R6G)
    lissamine rhodamine B sulfonyl chloride
    rhodamine (Rhod)
    rhodamine B
    rhodamine 110
    rhodamine 123
    rhodamine X isothiocyanate
    sulforhodamine B
    sulforhodamine 101
    sulfonyl chloride derivative of sulforhodamine 101 (Texas Red)
    N,N,N',N'-tetramethyl-6-carboxyrhodamine (TAMRA)
    tetramethyl rhodamine
    tetramethyl rhodamine isothiocyanate (TRITC)
riboflavin
rosolic acid
terbium chelate derivatives

5.4.1. Labeling of RNA

Depending on the particular intended use of the RNA amplification products, the RNA amplification products may be labeled. The RNA may be labeled with any art-known detectable marker, including but not limited to radioactive labels such as $^{32}P$, $^{35}S$, $^{3}H$, and the like; fluorophores; chemiluminescers; or enzymatic markers (e.g., as listed in Table 1).

Labeling of RNA is preferably accomplished by including one or more labeled NTPs in the in vitro transcription (IVT) reaction mixture. NTPs may be directly labeled with a radioisotope, such as $^{32}P$, $^{35}S$, $^{3}H$; radiolabeled NTPs are available from several sources, including New England Nuclear (Boston, Mass.) and Amersham. NTPs may be directly labeled with a fluorescent label such as Cy3 or Cy5. In one embodiment, biotinylated or allylamine-derivatized NTPs are incorporated during the IVT reaction and the resultant cRNAs are thereafter labeled, for example, by the addition of fluorophore-conjugated avidin, in the case of biotin, or the NHS ester of a fluorophore, in the case of allylamine. In another embodiment, fluorescently labeled NTPs may be incorporated during the IVT reaction, which fluorescently labels the resultant cRNAs directly.

RNA may be fluorescently labeled with fluorescently tagged nucleotides (e.g., fluorescently labeled ATP, UTP, GTP or CTP) that are incorporated into the antisense RNA product during the transcription step. Fluorescent moieties that may be used to tag nucleotides for producing labeled antisense RNA include: fluorescein, the cyanine dyes, such as Cy3, Cy5, Alexa 542, Bodipy 630/650, and the like. Other labels may also be employed as are known in the art. Exemplary fluorophore moieties that can be used as labels are listed in Table 1. The preferred label in the subject methods is a fluorophore, such as fluorescein isothiocyanate, lissamine, Cy3, Cy5, and rhodamine 110, with Cy3 and Cy5 particularly preferred.

Not only fluorophores, but also chemiluminescers and enzymes, among others, may be used as labels. In yet another embodiment, the RNA is labeled with an enzymatic marker that produces a detectable signal when a particular chemical reaction is conducted, such as alkaline phosphatase or horseradish peroxidase. Such enzymatic markers are preferably heat stable, so as to survive the denaturing steps of the amplification process.

RNA may also be indirectly labeled by incorporating a nucleotide linked covalently to a hapten or to a molecule such as biotin, to which a labeled avidin molecule may be bound, or digoxygenin, to which a labeled anti-digoxygenin antibody may be bound. RNA may be labeled with labeling moieties during chemical synthesis or the label may be attached after synthesis by methods known in the art.

Labeling of RNA is preferably accomplished by preparing cRNA that is fluorescently labeled with NHS-esters. Most preferably, labeling of RNA is accomplished in a two-step procedure in which allylamine-derivatized UTP (aa UTP) is incorporated during IVT. Following the IVT reaction, unincorporated nucleotides are removed and the allylamine-containing RNAs are conjugated to the N-hydroxysuccinimide (NHS) esters of Cy3 or Cy5.

In a preferred embodiment, 5-(3-Aminoallyl)uridine 5'-triphosphate is incorporated into the RNA amplification product during transcription and post-synthetically coupled to Cy-NHS, either Cy3-NHS or Cy5-NHS.

In a specific embodiment, a two-step method of preparing fluorescent-labeled cRNA may be used in two color hybridizations to DNA microarrays. Such a two-step method is disclosed in U.S. Ser. No. 09/411,074, filed Oct. 4, 1999, the disclosure of which is herein incorporated by reference. In one embodiment, aminoallyl (aa)-labeled nucleic acids are prepared by incorporation of aa-nucleotides. aa-UTP (Sigma A-5660) may be used for labeling cRNA. aa-cRNA is prepared using the Ambion MegaScript T7 RNA polymerase in vitro transcription kit, with aa-UTP substituted at 50–100% of the total UTP concentration. It is essential to remove all traces of amine-containing buffers such as Tris prior to derivatizing the aa-nucleic acids. aa-Nucleic acids prepared in enzymatic reactions are preferably cleaned up on appropriate QIAGEN columns: RNeasy® Mini kit (for RNA) or QIAquick PCR Purification kit (for DNA) (QIAGEN Inc.—USA, Valencia, Calif.). For the QIAGEN columns, samples are applied twice. For washes, 80% EtOH is preferably substituted for the buffer provided with the QIAGEN kit. Samples are eluted twice with 50 µl volumes of 70° C. $H_2O$. Alternatively (but less preferably), samples may be cleaned up by repeated cycles of dilution and concentration on Microcon-30 filters.

In a second step of the embodiment, α-nucleic acids are derivatized with NHS-esters, preferably Cy 3 or Cy 5. Preferably, 2–6 µg of aa-labeled nucleic acid are aliquoted into a microfuge tube, adjusting the total volume to 12 µl with $H_2O$. The NHS-ester is dissolved at a concentration of ~15 mM in anhydrous DMSO (~200 nmoles in 13 µl). 27 µl of 0.1 M sodium carbonate buffer, pH 9, are added. 12 µl of the dye mix (containing ~60 nmoles dye-NHS ester) are then immediately added to the aa-labeled nucleic acid (~6–20 pmoles of a 1 kb molecule). The samples are then incubated in the dark at 23° C. for 1 hour. The coupling reaction is stopped by adding 5 µl of a 4M solution of hydroxylamine. Incubation is continued at 23° C. for an additional 0.25 hr. Dye-coupled nucleic acid is separated from unincorporated dye on an RNeasy® Mini kit or QIAquick PCR Purification kit (QIAGEN Inc.—USA, Valencia, Calif.). Samples are washed with 80% EtOH instead of buffer, as described above, and eluted twice with 50 µl volumes of 70° C. $H_2O$.

The spectrum of the labeled nucleic acid is preferably measured from 220 nm-700 nm. The percent recovery of nucleic acid and molar incorporation of dye is calculated from extinction coefficients and absorbance values at $l_{max}$. Recovery of nucleic acid is typically ~80%. The mole percent of dye incorporated per nucleotide ranges from 1.5–5% of total nucleotides.

Often it is desired to compare gene expression in two different populations of cells, perhaps derived from different tissues or perhaps exposed to different stimuli. Such comparisons are facilitated by labeling the RNAs from one population with a first fluorophore and the RNAs from the other population, with a second fluorophore, where the two fluorophores have distinct emission spectra. Again, Cy3 and Cy5 are particularly preferred fluorophores for use in comparing gene expression between two different populations of cells.

5.5. Methods of Preparation of Source RNA

The source RNA may be obtained from a variety of different sources, typically a biological source. In specific embodiments, the biological source may be any of a variety of eukaryotic sources. Biological sources of interest may include sources derived from single-celled organisms such as yeast and multicellular organisms, including plants and animals, particularly mammals. Biological sources from multicellular organisms may be derived from particular organs or tissues of the multicellular organism, or from isolated cells derived therefrom. In obtaining the sample of RNA to be analyzed from its biological source, the source may be subjected to a number of different processing steps. Such processing steps might include tissue homogenization, cell isolation followed by cytoplasm extraction or isolation, nucleic acid extraction and the like. Such processing steps for isolating RNA from its biological source are known to those of skill in the art. For example, methods of isolating RNA from cells, tissues, organs or whole organisms are described in Sambrook et al. (1989), Molecular Cloning: A Laboratory Manual 2d Ed. (Cold Spring Harbor Press), incorporated herein by reference in its entirety. Alternatively, at least some of the initial steps of the subject methods may be performed in situ, as described in Eberwine (U.S. Pat. No. 5,514,545, entitled "Method for characterizing single cells based on RNA amplification for diagnostics and therapeutics," issued May 7, 1996), the disclosure of which is herein incorporated by reference.

Although the amplification methods of the invention can be adapted to amplify DNA, it is preferred to utilize the methods to amplify RNA from a population of cells. Total cellular RNA, cytoplasmic RNA, or poly(A)$^+$ RNA may be used, with poly(A)$^+$ RNA (mRNA) being preferred. Methods for preparing total and poly(A)$^+$ RNA are well known and are described generally in Sambrook et al. (1989, Molecular Cloning—A Laboratory Manual (2nd Ed.), Vols. 1–3, Cold Spring Harbor Laboratory, Cold Spring Harbor, N.Y.) and Ausubel et al., eds. (1994, Current Protocols in Molecular Biology, vol. 2, Current Protocols Publishing, New York), incorporated herein by reference in their entireties.

RNA may be isolated from eukaryotic cells by procedures that involve lysis of the cells and denaturation of the proteins contained therein. Cells of interest include wild-type cells, drug-exposed wild-type cells, modified cells, and drug-exposed modified cells.

Additional steps may be employed to remove DNA. Cell lysis may be accomplished with a nonionic detergent, followed by microcentrifugation to remove the nuclei and hence the bulk of the cellular DNA. In one embodiment, RNA is extracted from cells of the various types of interest using guanidinium thiocyanate lysis followed by CsCl centrifugation to separate the RNA from DNA (Chirgwin et al., 1979, Biochemistry 18:5294–5299). Poly(A)$^+$ RNA is selected by selection with oligo-dT cellulose (see Sambrook et al., 1989, *Molecular Cloning—A Laboratory Manual* (2nd Ed.), Vols. 1–3, Cold Spring Harbor Laboratory, Cold Spring Harbor, N.Y.). Alternatively, separation of RNA from DNA can be accomplished by organic extraction, for example, with hot phenol or phenol/chloroform/isoamyl alcohol.

If desired, RNase inhibitors may be added to the lysis buffer. Likewise, for certain cell types, it may be desirable to add a protein denaturation/digestion step to the protocol.

For many applications, it is desirable to preferentially enrich mRNA with respect to other cellular RNAs, such as transfer RNA (tRNA) and ribosomal RNA (rRNA). Most mRNAs contain a poly(A) tail at their 3' end. This allows them to be enriched by affinity chromatography, for example, using oligo(dT) or poly(U) coupled to a solid support, such as cellulose or Sephadex™ (see Ausubel et al., eds., 1994, *Current Protocols in Molecular Biology*, vol. 2, Current Protocols Publishing, New York). Once bound, poly(A)$^+$ mRNA is eluted from the affinity column using 2 mM EDTA/0.1% SDS.

The sample of RNA can comprise a plurality of different mRNA molecules, each different mRNA molecule having a different nucleotide sequence. In a specific embodiment, the mRNA molecules in the RNA sample comprise at least 100 different nucleotide sequences. More preferably, the mRNA molecules of the RNA sample comprise at least 500, 1,000, 5,000, 10,000, 20,000, 30,000, 40,000, 50,000, 60,000, 70,000, 80,000 90,000 or 100,000 different nucleotide sequences. In another specific embodiment, the RNA sample is a mammalian RNA sample, the mRNA molecules of the mammalian RNA sample comprising about 20,000 to 30,000 different nucleotide sequences.

In a specific embodiment, total RNA or mRNA from cells are used in the methods of the invention. The source of the RNA can be cells of a plant or animal, human, mammal, primate, non-human animal, dog, cat, mouse, rat, rabbit, bird, yeast, eukaryote, prokaryote, etc. In one embodiment, the method of the invention is used with a sample containing total mRNA or total RNA from $1 \times 10^6$ cells or less.

5.6. Methods for Determining Biological Response Profiles

This section provides some exemplary methods for measuring biological responses using cRNA amplified by methods of the invention. One of skill in the art would appreciate that this invention is not limited to the following specific methods for measuring the responses of a biological system, i.e., gene expression profiles. In particular, the presence of cRNA(s) of interest (and thus mRNA(s) of interest in the sample) can be detected or measured by procedures including, but not limited to, Northern blotting, the use of oligonucleotides tethered to beads as probes, or the use of polynucleotide microarrays.

In a specific embodiment of the invention, one or more labels is introduced into the RNA during the transcription step to facilitate gene expression profiling. Gene expression can be profiled in any of several ways, among which the preferred method is to probe a DNA microarray with the labeled RNA transcripts generated above. A DNA microarray, or chip, is a microscopic array of DNA fragments or synthetic oligonucleotides, disposed in a defined pattern on a solid support, wherein they are amenable to analysis by standard hybridization methods (Schena, *BioEssays* 18: 427, 1996).

The DNA in a microarray may be derived from genomic or cDNA libraries, from fully sequenced clones, or from partially sequenced cDNAs known as expressed sequence tags (ESTs). Methods for obtaining such DNA molecules are generally known in the art (see, e.g., Ausubel et al., eds., 1994, *Current Protocols in Molecular Biology*, vol. 2, Current Protocols Publishing, New York). Alternatively, oligonucleotides may be synthesized by conventional methods, such as phosphoramidite-based synthesis.

Gene expression profiling can be done for purposes of screening, diagnosis, staging a disease, and monitoring response to therapy, as well as for identifying genetic targets of drugs and of pathogens.

5.6.1. Transcript Assay Using DNA Arrays

This invention is particularly useful for the analysis of gene expression profiles. For expression profiling, DNA microarrays are typically probed using mRNA, extracted and amplified from the cells whose gene expression profile it is desired to analyze, using the random-primed RT-IVT amplification method of the invention. To facilitate comparison between any two samples of interest, the polynucleotides representing the mRNA transcripts present in a cell are typically labeled separately with fluorescent dyes that emit at different wavelengths. Some embodiments of this invention are based on measuring the transcriptional rate of genes.

The transcriptional rate can be measured by techniques of hybridization to arrays of nucleic acid or nucleic acid mimic probes, described in the next subsection, or by other gene expression technologies, such as those described in the subsequent subsection. However measured, the result is either the absolute, relative amounts of transcripts or response data including values representing RNA abundance ratios, which usually reflect DNA expression ratios (in the absence of differences in RNA degradation rates).

In various alternative embodiments of the present invention, aspects of the biological state other than the transcriptional state, such as the translational state, the activity state, or mixed aspects can be measured.

Preferably, measurement of the transcriptional state is made by hybridization to transcript arrays, which are described in this subsection. Certain other methods of transcriptional state measurement are described later in this subsection.

In a preferred embodiment the present invention makes use of "transcript arrays" (also called herein "microarrays"). Transcript arrays can be employed for analyzing the transcriptional state in a biological sample and especially for measuring the transcriptional states of a biological sample exposed to graded levels of a drug of interest or to graded perturbations to a biological pathway of interest.

In one embodiment, transcript arrays are produced by hybridizing detectably labeled polynucleotides representing the mRNA transcripts present in a cell (e.g., fluorescently labeled cRNA that is amplified by the methods of the present invention) to a microarray. A microarray is a surface with an ordered array of binding (e.g., hybridization) sites for products of many of the genes in the genome of a cell or organism, preferably most or almost all of the genes. Microarrays can be made in a number of ways, of which several are described below. However produced, microarrays share certain preferred characteristics: The arrays are reproducible, allowing multiple copies of a given array to be produced and easily compared with each other. Preferably the microarrays are small, usually smaller than 5 cm$^2$, and they are made from materials that are stable under binding (e.g., nucleic acid hybridization) conditions. A given binding site or unique set of binding sites in the microarray will specifically bind the product of a single gene in the cell.

Although there may be more than one physical binding site (hereinafter "site") per specific mRNA for the sake of clarity the discussion below will assume that there is a single site.

In one embodiment, the microarray is an array of polynucleotide probes, the array comprising a support with at least one surface and at least 100 different polynucleotide probes, each different polynucleotide probe comprising a different nucleotide sequence and being attached to the surface of the support in a different location on the surface. Preferably, the nucleotide sequence of each of the different polynucleotide probes is in the range of 40 to 80 nucleotides in length. More preferably, the nucleotide sequence of each of the different polynucleotide probes is in the range of 50 to 70 nucleotides in length. Even more preferably, the nucleotide sequence of each of the different polynucleotide probes is in the range of 50 to 60 nucleotides in length.

In specific embodiments, the array comprises polynucleotide probes of at least 2,000, 4,000, 10,000, 15,000, 20,000, 50,000, 80,000, or 100,000 different nucleotide sequences.

In another embodiment, the nucleotide sequence of each polynucleotide probe in the array is specific for a particular target polynucleotide sequence. In yet another embodiment, the target polynucleotide sequences comprise expressed polynucleotide sequences of a cell or organism.

In a specific embodiment, the cell or organism is a mammalian cell or organism. In another specific embodiment, the cell or organism is a human cell or organism.

In specific embodiments, the nucleotide sequences of the different polynucleotide probes of the array are specific for at least 50%, at least 75%, at least 80%, at least 85%, at least 90%, at least 95%, or at least 99% of the genes in the genome of the cell or organism. Most preferably, the nucleotide sequences of the different polynucleotide probes of the array are specific for all of the genes in the genome of the cell or organism.

In specific embodiments, the polynucleotide probes of the array hybridize specifically and distinguishably to at least 10,000, to at least 20,000, to at least 50,000, different polynucleotide sequences, to at least 80,000, or to at least 100,000 different polynucleotide sequences.

In other specific embodiments, the polynucleotide probes of the array hybridize specifically and distinguishably to at least 90%, at least 95%, or at least 99% of the genes or gene transcripts of the genome of a cell or organism. Most preferably, the polynucleotide probes of the array hybridize specifically and distinguishably to the genes or gene transcripts of the entire genome of a cell or organism.

In specific embodiments, the array has at least 100, at least 250, at least 1,000, or at least 2,500 probes per 1 cm$^2$, preferably all or at least 25% or 50% of which are different from each other.

In another embodiment, the array is a positionally addressable array (in that the sequence of the polynucleotide probe at each position is known).

In another embodiment, the nucleotide sequence of each polynucleotide probe in the array is a DNA sequence. In another embodiment, the DNA sequence is a single-stranded DNA sequence. The DNA sequence may be, e.g., a cDNA sequence, or a synthetic sequence.

When cRNA complementary to the RNA of a cell is made and hybridized to a microarray under suitable hybridization conditions, the level of hybridization to the site in the array corresponding to any particular gene will reflect the prevalence in the cell of mRNA transcribed from that gene. For example, when detectably labeled (e.g., with a fluorophore) cRNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

In preferred embodiments, cRNAs from two different cells are hybridized to the binding sites of the microarray. In the case of drug responses one biological sample is exposed to a drug and another biological sample of the same type is not exposed to the drug. In the case of pathway responses one cell is exposed to a pathway perturbation and another cell of the same type is not exposed to the pathway perturbation. The cRNA derived from each of the two cell types are differently labeled so that they can be distinguished. In one embodiment, for example, cRNA from a cell treated with a drug (or exposed to a pathway perturbation) is synthesized using a fluorescein-labeled NTP, and cRNA from a second cell, not drug-exposed, is synthesized using a rhodamine-labeled NTP. When the two cRNAs are mixed and hybridized to the microarray, the relative intensity of signal from each cRNA set is determined for each site on the array, and any relative difference in abundance of a particular mRNA detected.

In the example described above, the cRNA from the drug-treated (or pathway perturbed) cell will fluoresce green when the fluorophore is stimulated and the cRNA from the untreated cell will fluoresce red. As a result, when the drug treatment has no effect, either directly or indirectly, on the relative abundance of a particular mRNA in a cell, the mRNA will be equally prevalent in both cells and, upon reverse transcription, red-labeled and green-labeled cRNA will be equally prevalent. When hybridized to the microarray, the binding site(s) for that species of RNA will emit wavelengths characteristic of both fluorophores (and appear brown in combination). In contrast, when the drug-exposed cell is treated with a drug that, directly or indirectly, increases the prevalence of the mRNA in the cell, the ratio of green to red fluorescence will increase. When the drug decreases the mRNA prevalence, the ratio will decrease.

The use of a two-color fluorescence labeling and detection scheme to define alterations in gene expression has been described, e.g., in Schena et al., 1995, Science 270:467–470, which is incorporated by reference in its entirety for all purposes. An advantage of using cRNA labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. However, it will be recognized that it is also possible to use cRNA from a single cell, and compare, for example, the absolute amount of a particular mRNA in, e.g., a drug-treated or pathway-perturbed cell and an untreated cell.

5.6.2. Preparation of Microarrays

Microarrays are known in the art and consist of a surface to which probes that correspond in sequence to gene products (e.g., cDNAs, mRNAs, cRNAs, polypeptides, and fragments thereof), can be specifically hybridized or bound at a known position. In one embodiment, the microarray is an array (i.e., a matrix) in which each position represents a discrete binding site for a product encoded by a gene (e.g., a protein or RNA), and in which binding sites are present for products of most or almost all of the genes in the organism's genome. In a preferred embodiment, the "binding site" (hereinafter, "site") is a nucleic acid or nucleic acid analogue to which a particular cognate cRNA can specifically hybridize. The nucleic acid or analogue of the binding site can be, e.g., a synthetic oligomer, a full-length cRNA, a less-than full length cRNA, or a gene fragment.

In one embodiment, the microarray contains binding sites for products of all or almost all genes in the target organism's genome. This microarray will have binding sites corresponding to at least about 50% of the genes in the genome, often at least about 75%, more often at least about 85%, even more often more than about 90%, and most often at least about 99%.

Such comprehensiveness, however, is not necessarily required. In another embodiment, the microarray contains binding sites for products of human genes. This microarray will have binding sites corresponding to at least about 5–10% of the genes in the genome, preferably at least about 10–15%, and more preferably at least about 40%.

Preferably, the microarray has binding sites for genes relevant to the action of a drug of interest or in a biological pathway of interest. A "gene" is identified as an open reading frame (ORF) of preferably at least 50, 75, or 99 amino acids from which a messenger RNA is transcribed in the organism (e.g., if a single cell) or in some cell in a multicellular organism. The number of genes in a genome can be estimated from the number of mRNAs expressed by the organism, or by extrapolation from a well-characterized portion of the genome. When the genome of the organism of interest has been sequenced, the number of ORFs can be determined and mRNA coding regions identified by analysis of the DNA sequence. For example, the *Saccharomyces cerevisiae* genome has been completely sequenced and is reported to have approximately 6275 open reading frames (ORFs) longer than 99 amino acids. Analysis of these ORFs indicates that there are 5885 ORFs that are likely to specify protein products (Goffeau et al., 1996, Science 274:546–567, which is incorporated by reference in its entirety for all purposes). In contrast, the human genome is estimated to contain approximately $10^5$ genes.

5.6.3. Preparation of Nucleic Acids for Microarrays

As noted above, the "binding site" to which a particular cognate cRNA specifically hybridizes is usually a nucleic acid or nucleic acid analogue attached at that binding site. In one embodiment, the binding sites of the microarray are DNA polynucleotides corresponding to at least a portion of each gene in an organism's genome. These DNAs can be obtained by, e.g., polymerase chain reaction (PCR) amplification of gene segments from genomic DNA, cDNA (e.g., by reverse transcription or RT-PCR), or cloned sequences. Nucleic acid amplification primers are chosen, based on the known sequence of the genes or cDNA, that result in amplification of unique fragments (i.e., fragments that do not share more than 10 bases of contiguous identical sequence with any other fragment on the microarray). Computer programs are useful in the design of primers with the required specificity and optimal amplification properties. See, e.g., Oligo version 5.0 (National Biosciences). In the case of binding sites corresponding to very long genes, it will sometimes be desirable to amplify segments near the 3' end of the gene so that when oligo-dT primed cDNA probes are hybridized to the microarray, less-than-full length probes will bind efficiently. Typically each gene fragment on the microarray will be between about 50 bp and about 2000 bp, more typically between about 100 bp and about 1000 bp, and usually between about 300 bp and about 800 bp in length.

Nucleic acid amplification methods are well known and are described, for example, in Innis et al., eds., 1990, *PCR Protocols: A Guide to Methods and Applications*, Academic Press Inc., San Diego, Calif., which is incorporated by reference in its entirety for all purposes. It will be apparent that computer controlled robotic systems are useful for isolating and amplifying nucleic acids.

An alternative means for generating the nucleic acid for the microarray is by synthesis of synthetic polynucleotides or oligonucleotides, e.g., using N-phosphonate or phosphoramidite chemistries (e.g., Froehler et al., 1986, Nucleic Acid Res 14:5399–5407). Synthetic sequences are between about 15 and about 100 bases in length, preferably between about 20 and about 50 bases.

In some embodiments, synthetic nucleic acids include non-natural bases, e.g., inosine. Where the particular base in a given sequence is unknown or is polymorphic, a universal base, such as inosine or 5-nitroindole, may be substituted. Additionally, it is possible to vary the charge on the phosphate backbone of the oligonucleotide, for example, by thiolation or methylation, or even to use a peptide rather than a phosphate backbone. The making of such modifications is within the skill of one trained in the art.

As noted above, nucleic acid analogues may be used as binding sites for hybridization. An example of a suitable nucleic acid analogue is peptide nucleic acid (see, e.g., Egholm et al., 1993, Nature 365:566–568; see also U.S. Pat. No. 5,539,083, Cook et al., entitled "Peptide nucleic acid combinatorial libraries and improved methods of synthesis," issued July 23, 1996).

In an alternative embodiment, the binding (hybridization) sites are made from plasmid or phage clones of genes, cDNAs (e.g., expressed sequence tags), or inserts therefrom (Nguyen et al., 1995, Genomics 29:207–209). In yet another embodiment, the polynucleotide of the binding sites is RNA.

5.6.4. Attaching Nucleic Acids to the Solid Surface

The nucleic acid or analogue are attached to a solid support, which may be made from glass, silicon, plastic (e.g., polypropylene, nylon, polyester), polyacrylamide, nitrocellulose, cellulose acetate or other materials. In general, non-porous supports, and glass in particular, are preferred. The solid support may also be treated in such a way as to enhance binding of oligonucleotides thereto, or to reduce non-specific binding of unwanted substances thereto. Preferably, the glass support is treated with polylysine or silane to facilitate attachment of oligonucleotides to the slide.

Methods of immobilizing DNA on the solid support may include direct touch, micropipetting (Yershov et al., Proc. Natl. Acad. Sci. USA (1996) 93(10):4913–4918), or the use of controlled electric fields to direct a given oligonucleotide to a specific spot in the array (U.S. Pat. No. 5,605,662, Heller et al., entitled "Active programmable electronic devices for molecular biological analysis and diagnostics," issued Feb. 25, 1997). DNA is typically immobilized at a density of 100 to 10,000 oligonucleotides per $cm^2$ and preferably at a density of about 1000 oligonucleotides per $cm^2$.

A preferred method for attaching the nucleic acids to a surface is by printing on glass plates, as is described generally by Schena et al., 1995, Science 270:467–470. This method is especially useful for preparing microarrays of cDNA. (See also DeRisi et al., 1996, Nature Genetics 14:457–460; Shalon et al., 1996, Genome Res. 6:639–645; and Schena et al., Proc. Natl. Acad. Sci. USA, 1996, 93(20):10614–19.)

In a preferred alternative to immobilizing pre-fabricated oligonucleotides onto a solid support, it is possible to synthesize oligonucleotides directly on the support (Maskos et al., Nucl. Acids Res. 21: 2269–70, 1993; Fodor et al., Science 251: 767–73, 1991; Lipshutz et al., 1999, Nat.

Genet. 21(1 Suppl):20–4). Among methods of synthesizing oligonucleotides directly on a solid support, particularly preferred methods are photolithography (see Fodor et al., Science 251: 767–73, 1991; McGall et al., Proc. Natl. Acad. Sci. (USA) 93: 13555–60, 1996) and piezoelectric printing (Lipshutz et al., 1999, Nat. Genet. 21(1 Suppl):20–4), with the piezoelectric method most preferred.

In one embodiment, a high-density oligonucleotide array is employed. Techniques are known for producing arrays containing thousands of oligonucleotides complementary to defined sequences, at defined locations on a surface using photolithographic techniques for synthesis in situ (see, Fodor et al., 1991, Science 251:767–773; Pease et al., 1994, Proc. Natl. Acad. Sci. USA 91:5022–5026; Lockhart et al., 1996, Nature Biotechnol. 14:1675–80; U.S. Pat. No. 5,578, 832, Trulson et al., entitled "Method and apparatus for imaging a sample on a device," issued Nov. 26, 1996; U.S. Pat. No. 5,556,752, Lockhart et al., entitled "Surface-bound, unimolecular, double-stranded DNA," issued Sep. 17, 1996; and U.S. Pat. No. 5,510,270, Fodor et al., entitled "Synthesis and screening of immobilized oligonucleotide arrays," issued Apr. 23, 1996; each of which is incorporated by reference in its entirety for all purposes) or other methods for rapid synthesis and deposition of defined oligonucleotides (Lipshutz et al., 1999, Nat. Genet. 21(1 Suppl):20–4.)

When these methods are used, oligonucleotides (e.g., 20-mers) of known sequence are synthesized directly on a surface such as a derivatized glass slide. Usually, the array produced contains multiple probes against each target transcript. Oligonucleotide probes can be chosen to detect alternatively spliced mRNAs or to serve as various type of control.

In a particularly preferred embodiment, microarrays of the invention are manufactured by means of an ink jet printing device for oligonucleotide synthesis, e.g., using the methods and systems described by Blanchard in International Patent Publication No. WO 98/41531, published Sep. 24, 1998; Blanchard et al., 1996, Biosensors and Bioeletronics 11:687–690; Blanchard, 1998, in Synthetic DNA Arrays in Genetic Engineering, Vol. 20, J. K. Setlow, Ed., Plenum Press, New York at pages 111–123; U.S. Pat. No. 6,028,189 to Blanchard. Specifically, the oligonucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes).

Other methods for making microarrays, e.g., by masking (Maskos and Southern, 1992, Nuc. Acids Res. 20:1679–1684), may also be used. In principal, any type of array, for example, dot blots on a nylon hybridization membrane (see Sambrook et al., 1989, Molecular Cloning—A Laboratory Manual (2nd Ed.), Vols. 1–3, Cold Spring Harbor Laboratory, Cold Spring Harbor, N.Y.), could be used, although, as will be recognized by those of skill in the art, very small arrays will be preferred because hybridization volumes will be smaller.

5.6.5. Hybridization to Microarrays

Nucleic acid hybridization and wash conditions are optimally chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g. Shalon et al., 1996, Genome Research 6:639–645, and Chee et al., 1996, Science 274:610–614).

Optimal hybridization conditions will depend on the length (e.g., oligomer versus polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al. (1989, Molecular Cloning—A Laboratory Manual (2nd Ed.), Vols. 1–3, Cold Spring Harbor Laboratory, Cold Spring Harbor, N.Y.) and in Ausubel et al. (1987, Current Protocols in Molecular Biology, Greene Publishing, Media, Pa., and Wiley-Interscience, New York). When the cDNA microarrays of Schena et al. (1996, Proc. Natl. Acad. Sci. USA, 93:10614–19) are used, typical hybridization conditions are hybridization in 5×SSC plus 0.2% SDS at 65° C. for 4 hours followed by washes at 25° C. in low stringency wash buffer (1×SSC plus 0.2% SDS) followed by 10 minutes at 25° C. in high stringency wash buffer (0.1×SSC plus 0.2% SDS) (Schena et al., 1996, Proc. Natl. Acad. Sci. USA, 93:10614–19). Useful hybridization conditions are also provided in, e.g., Tijssen, 1993, Hybridization With Nucleic Acid Probes, Elsevier Science Publishers B.V., Amsterdam and New York, and Kricka, 1992, Nonisotopic DNA Probe Techniques, Academic Press, San Diego, Calif.

Although simultaneous hybridization of differentially labeled mRNA samples is preferred, it is also possible to use a single label and to perform hybridizations sequentially rather than simultaneously.

5.6.6. Signal Detection and Data Analysis

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, Genome Research 6:639–645, which is incorporated by reference in its entirety for all purposes). In a preferred embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Shalon et al., 1996, Genome Res. 6:639–645 and in other references cited herein. Alternatively, the fiber-optic bundle described by Ferguson et al., 1996, Nature Biotechnol. 14:1681–1684, may be used to monitor mRNA abundance levels at a large number of sites simultaneously.

Signals are recorded and, in a preferred embodiment, analyzed by computer, e.g., using a 12 bit analog to digital board. In one embodiment the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA in two biological samples is scored as a perturbation and its magnitude determined (i.e., the abundance is different in the two sources of mRNA tested), or as not perturbed (i.e., the relative abundance is the same). In various embodiments, a difference between the two sources of RNA of at least a factor of about 25% (RNA from one source is 25% more abundant in one source than the other source), more usually about 50%, even more often by a factor of about 2 (twice as abundant), 3 (three times as abundant) or 5 (five times as abundant) is scored as a perturbation.

Preferably, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

In one embodiment, two samples, each labeled with a different fluor, are hybridized simultaneously to permit differential expression measurements. If neither sample hybridizes to a given spot in the array, no fluorescence will be seen. If only one hybridizes to a given spot, the color of the resulting fluorescence will correspond to that of the fluor used to label the hybridizing sample (for example, green if the sample was labeled with Cy3, or red, if the sample was labeled with Cy5). If both samples hybridize to the same spot, an intermediate color is produced (for example, yellow if the samples were labeled with fluorescein and rhodamine). Then, applying methods of pattern recognition and data analysis known in the art, it is possible to quantify differences in gene expression between the samples. Methods of pattern recognition and data analysis are described in e.g., co-pending U.S. patent applications Ser. No. 09/179,569 filed on Oct. 27, 1998, by Friend et al.; Ser. No. 09/220,142 filed on Dec. 23, 1998, by Stoughton et al.; Ser. No. 09/220,275 filed on Dec. 23, 1998, by Friend et al.; International Publication WO 00/24936, dated May 4, 2000, which are incorporated by reference herein in their entireties.

5.7. Diagnostic Methods

The random-primed RT-IVT methods of the invention have use in nucleic acid amplification reactions to generate sufficient quantities of nucleic acid for detection of a specific nucleic acid of interest. Accordingly, the methods of the invention can be used in methods of diagnosis, for example, in amplifying a sequence (e.g., genomic) of an infectious disease agent, e.g., of human disease including but not limited to viruses, bacteria, parasites, and fungi, thereby diagnosing the presence of the infectious agent in a sample of nucleic acid from a patient. The nucleic acid of interest can be genomic or cDNA or mRNA, or can be synthetic, human or animal, or of a microorganism, etc. In another embodiment that can be used in the diagnosis or prognosis of a disease or disorder, the nucleic acid of interest is a wild type human genomic or RNA or cDNA sequence, mutation of which is implicated in the presence of a human disease or disorder, or alternatively, can be the mutated sequence. By way of example, the mutation can be an insertion, substitution, and/or deletion of one or more nucleotides, or a translocation.

5.8. Kits for the Amplification and Detection of Selected Target Nucleotide Sequences The present invention also provides kits for the linear amplification of RNA, and, for example, detection or measurement of nucleic acid amplification products and for determining the responses or state of a biological sample. Such a kit may comprise containers, each with one or more of the various reagents (typically in concentrated form) utilized in the methods of the invention, including, for example, buffers, the appropriate nucleotide triphosphates (e.g., dATP, dCTP, dGTP, dTTP, ATP, CTP, GTP and UTP), reverse transcriptase, RNA polymerase specific to the RNA polymerase promoter, and the random promoter-primers and primers of the present invention. Optionally also present in the kit is a reverse transcriptase inhibitor, where, in many embodiments, the inhibitor is at least ddNTP or a combination of ddNTPs, e.g., ddATP and/or ddGTP. A set of instructions for use of kit components in an mRNA amplification method of the present invention, will also be typically included.

In a specific embodiment, the kit comprises one or more primer oligonucleotides of the invention, such as a RNA polymerase promoter-containing primer, including but not limited to a set of random RNA polymerase promoter-containing primers and/or a set of random primers, in one or more containers. The kit can comprise for example, a random T7-poly dN primer set, a T7-poly dT primer, and/or a random poly dN primer set. The kit can further comprise additional components for carrying out the amplification reactions of the invention, such as reverse transcriptase and RNA polymerase. Where the target nucleic acid sequence being amplified is one implicated in disease or disorder, the kit can be used for diagnosis or prognosis.

Oligonucleotides in containers can be in any form, e.g., lyophilized, or in solution (e.g., a distilled water or buffered solution), etc. Oligonucleotides ready for use in the same amplification reaction can be combined in a single container or can be in separate containers.

The kit optionally further comprises a control nucleic acid, and/or a microarray, and/or means for stimulating and detecting fluorescent light emissions from fluorescently labeled RNA, and/or expression profile projection and analysis software capable of being loaded into the memory of a computer system. The kit optionally further provides means for stimulating and detecting fluorescent light emissions, e.g., a fluorescence plate reader or a combination thermocycler-plate-reader to perform the analysis.

5.8.1. Analytic Kit Implementation

In a preferred embodiment, the methods of this invention can be implemented by use of kits containing oligonucleotide primers of the invention and microarrays. The microarrays contained in such kits comprise a solid phase, e.g., a surface, to which probes are hybridized or bound at a known location of the solid phase. Preferably, these probes consist of nucleic acids of known, different sequence, with each nucleic acid being capable of hybridizing to a RNA species or to a cDNA species derived therefrom. In particular, the probes contained in the kits of this invention are nucleic acids capable of hybridizing specifically to nucleic acid sequences derived from RNA species that are known to increase or decrease in response to perturbations to the particular protein whose activity is determined by the kit. The probes contained in the kits of this invention preferably substantially exclude nucleic acids that hybridize to RNA species that are not increased in response to perturbations to the particular protein whose activity is determined by the kit.

In another preferred embodiment, a kit of the invention further contains expression profile projection and analysis software capable of being loaded into the memory of a computer system. An example of such a system is described in co-pending U.S. patent application Ser. No. 09/220,276, by Bassett, Jr. et al., filed Dec. 23, 1998, which is incorporated herein by reference in its entirety. Preferably, the expression profile analysis software contained in a kit of this invention, is essentially identical to the expression profile analysis software 512 described in U.S. patent application Ser. No. 09/220,276.

Alternative kits for implementing the analytic methods of this invention will be apparent to one of skill in the art and are intended to be comprehended within the accompanying claims. In particular, the accompanying claims are intended to include the alternative program structures for implementing the methods of this invention that will be readily apparent to one of skill in the art.

The following experimental examples are offered by way of illustration and not by way of limitation.

6. EXAMPLE 1 cDNA Synthesis and RNA Amplification for the Preparation of CY3- and CY5-Labeled RNA Targets for Gene Expression Monitoring This example demonstrates that using the random-primed RT-IVT method of the invention, linear amplification of mRNA to can be used to produce unbiased antisense RNA profiles. The results of an mRNA amplification produced using the random-primed RT-IVT method of the invention were compared with results obtained using the mRNA amplification method disclosed in Shannon (U.S. Pat. No. 6,132,997, entitled "Method for linear mRNA amplification," issued Oct. 17, 2000). Using the random-primed RT-IVT method, poly-A$^+$ RNA was converted to double-stranded cDNA using degenerate random primers comprising a T7 RNA polymerase promoter sequence (T7-dN$_9$) to prime first strand cDNA synthesis and degenerate random primers (dN$_6$) to prime second strand cDNA synthesis to yield a double-stranded cDNA that is recognized by T7 RNA polymerase. The double-stranded cDNA was then transcribed into antisense RNA by T7 RNA polymerase in the presence of a reverse transcriptase that was rendered incapable of RNA-dependent DNA polymerase activity during this transcription step by heat inactivation. 5-(3-Aminoallyl)uridine 5'-triphosphate was incorporated into the antisense RNA during transcription and post-synthetically labeled with Cy3-NHS or Cy5-NHS. Linear amplification extents of at least 100-fold and labeling efficiencies of approximately 3% were achieved using this method.

6.1. Materials and Methods

Total RNA was isolated from Jurkat and K562 cell lines. Poly-A$^+$ RNA was isolated from the total RNA to provide the initial source mRNA used in the experiment.

cDNA Synthesis Reagents:
1. mRNA, 0.2 mg.
2. DNA T7-dN$_9$ (20 µM): (5') AAT TAA TAC GAC TCA CTA TAG GGA GAT NNN NNN NNN (3') (N=A, T, C or G) (SEQ ID NO.: 1)
3. MMLV Reverse Transcriptase (50 U/µl), Epicentre P/N M4425H
4. RNAGuard™, Pharmacia P/N 27-0815-01
5. 5× First Strand Buffer: 250 mM Tris-HCl, pH 8.3, 15 mM MgCl$_2$, 375 mM KCl, Life Technologies P/N 18057-018
6. 100 mM DTT* (*supplied with MMLV Reverse Transcriptase, Epicentre)
7. dNTPs (10 mM each), diluted from Pharmacia P/N 2702035-01
8. ultraPURE distilled water, DNAse, RNAse Free, Life Technologies, Cat # 10977-015
9. pdN$_6$ (200 ng/µl), diluted from Amersham Pharmacia Biotech P/N 27-2166-01

Transcription Reagents:
1. T7 RNA Polymerase (2500 units/µl), Epicentre P/N TU950K
2. RNAGuard™, Pharmacia P/N 27-0815-01
3. Inorganic Pyrophosphatase (200 U/ml), New England Biolabs, #M0296S.
4. 5× Transcription Buffer: 0.2 M Tris-HCl, pH 7.5, 50 mM NaCl, 30 mM MgCl$_2$, 10 mM spermidine, Epicentre PIN BP1001
5. 100 mM DTT, Epicentre PIN BP1001
6. MgCl$_2$ (200 mM), diluted from Sigma P/N M-1028
7. NTPs (25 mM ATP, GTP, CTP, 6 mM UTP), diluted from Pharmacia P/N 27-2025-01
8. 5-(3-Aminoallyl)uridine 5'-triphosphate (75 mM), Sigma P/N A-5660
9. ultraPURE distilled water, DNAse, RNAse Free, Life Technologies, P/N 10977-015

Purification and Labeling Reagents:
1. RNeasy® Mini Kit (250), QIAGEN Inc., P/N 74106
2. Carbonate-Bicarbonate Buffer capsules, Sigma, PIN C-3041
3. Hydrochloric acid, Fisher, P/N A508-500
4. Anhydrous MSO (methyl sulfoxide, also known as DMSO, dimethyl sulfoxide), Aldrich, PIN 27,685-5
5. Cy3-NHS dye pack, Amersham, P/N PA23001
6. Cy5-NHS dye pack, Amersham, P/N PA25001
7. Hydroxylamine ("HA"), Sigma, P/N H-2391

Other Materials:
1. Pipetman micropipettors, (P-10, P-20, P-200, P-1000), or equivalent
2. Sterile, nuclease-free 1.5 ml microcentrifuge tubes
3. Sterile, nuclease-free aerosol-barrier pipet tips
4. Thermal Cycler Reagent Preparation:
1. dNTPs (10 mM each) Thaw dNTP stocks (100 mM) and place on ice. Add 10 µl each dNTP to 60 µl nuclease-free water. Store frozen.
2. pdN$_6$ (200 ng/µl) Add 663 µl nuclease-free water to lyophilized sample (50 A260 units or approximately 1325 µg) for 2.0 µg/µl. Add 10 µl pdN$_6$ (2.0 µg/µl) to 90 µl nuclease-free water for 200 ng/µl. Store frozen.
3. 200 mM MgCl$_2$ Add 100 µl of 1 M MgCl$_2$ to 400 µl nuclease-free water. Store frozen.
4. NTPs (25 mM ATP, GTP, CTP, 6.0 mM UTP) Thaw NTP stocks (100 mM) and place on ice. Combine 125 µl ATP, 125 µl GTP, 125 µl CTP, 30 µl UTP and 95 µl nuclease-free water. Store frozen.
5. aa UTP (75 mM) Dissolve 5 mg in 125 µl water.
6. Anhydrous MSO should be stored with a molecular sieve to absorb water.

Procedure:

To prevent contamination of reactions by ribonucleases, laboratory gloves were worn and dedicated solutions and pipettors with nuclease-free, aerosol-resistant tips were used.

Amplified RNA preparations were prepared in batches of no less than 6 to minimize errors associated with pipetting small volumes of enzyme solutions. The procedure below specifies reagent volumes for 1 reaction; for 6 reactions, the specified volumes were multiplied by 6.5.

1. Add 0.2 µg of source mRNA to reaction tube. Add 1.0 µl DNA T7-dN$_9$ (20 µM) and bring total sample volume to 10.5 µl in nuclease-free water.
2. Incubate at 65° C. for 10 min to denature primer and template. Move reaction tubes to ice. Store reactions tubes on ice for 5 min.
3. Mix the following components and maintain on ice.

cDNA Mix

| Component | Volume (µl) |
| --- | --- |
| 5x First Strand Buffer | 4.0 |
| 100 mM DTT | 2.0 |
| dNTPs (10 mM each) | 1.0 |
| pdN$_6$ (200 ng/µl) | 1.0 |
| MMLV-RT (50 U/µl) | 1.0 |
| RNAGuard ™ (36 U/µl) | 0.5 |
| Volume of cDNA Mix | 9.5 |

4. Aliquot 9.5 µl of cDNA Mix into each sample tube. Incubate cDNA synthesis reaction at 40° C. for 120 min.

Composition of cDNA Synthesis Reaction

| Component | Final concentration or amount |
| --- | --- |
| poly-A$^+$ RNA | 200 ng |
| DNA T7T18VN | 1 µM |
| Tris-HCl, pH 8.3 | 50 mM |
| MgCl$_2$ | 3.0 mM |
| KCl | 75 mM |
| DTT | 10 mM |
| dNTPs | 0.5 mM each |
| MMLV-RT | 50 U |
| RNAGuard ™ | 18 U |
| Total reaction volume | 20 µl |

Incubate reaction tubes at 65° C. for 15 min. This inactivates the reverse transcriptase activity of MMLV prior to the IVT step. Move reaction tubes to ice. Store reaction tubes on ice for 5 min.

5. Immediately before use, mix the following components in the order indicated at room temperature:

Transcription Mix

| Component | Volume (µl) |
| --- | --- |
| Nuclease-free water | 22.8 |
| 5x Transcription Buffer | 16 |
| 100 mM DTT | 6.0 |
| NTPs (25 mM A, G, C, 6.0 mM UTP) | 8.0 |
| aa UTP (75 mM) | 2.0 |
| 200 mM MgCl$_2$ | 3.3 |
| RNAGuard ™ (36 U/µl) | 0.5 |
| Inorganic Pyrophosphatase (200 U/ml) | 0.6 |
| T7 RNA polymerase (2500 U/µl) | 0.8 |
| Volume of Transcription Mix | 60 |

6. Aliquot 60 µl of Transcription Mix into each sample tube. Incubate transcription reactions at 40° C. for 16 hrs.

Composition of Transcription Reaction

| Component | Final concentration or amount |
| --- | --- |
| Double-strand cDNA | Approximately 400 ng |
| Tris-HCl, pH 7.5 | 52 mM |
| MgCl$_2$ | 15 mM |
| KCl | 19 mM |
| NaCl | 10 mM |
| Spermidine | 2 mM |
| DTT | 10 mM |
| ATP, GTP, CTP | 2.5 mM each |
| UTP | 0.6 mM |
| aa UTP | 1.9 mM |
| T7 RNA polymerase | 2000 U |
| RNAGuard ™ | 18 U |
| Inorganic pyrophosphatase | 0.12 U |
| Total reaction volume | 80 µl |

7. RNeasy® (QIAGEN Inc.) Purification of reactions:
Add 20 µl water to 80 µl reaction tube.
Transfer to mixing tube.
Add 350 µl RLT buffer (QIAGEN Inc.) (plus 2-β-mercaptoethanol), mix well.
Add 250 µl 100% EtOH, mix well.
Transfer to RNeasy® column.
Spin 30 seconds in microfuge, 10 K.
Transfer column to new collection tube.
Add 7001 µl 80% EtOH.
Spin 30 seconds in microfuge, 10 K.
Discard flow through.
Add 700 µl 80% EtOH.
Spin 30 seconds in microfuge, 10 K.
Transfer column to new collection tube.
Spin 2 minutes, 14 K to dry filter.
Place column in microfuge tube.
Add 55 µl of nuclease-free water to filter. Let sit 1 minute.
Spin 14 K, 2 minutes.
Add 55 µl of nuclease-free water to filter. Let sit 1 minute.
Spin 14 K, 2 minutes.

To quantitate the yield of amplified RNA product, remove a 10.0 µl aliquot of the product and dilute into 90 µl dH$_2$O. Add samples to a Costar UV-transparent plate and measure A260, A280 using a Spectramax (GRM Reader) and template for whichever lot of plates you are using. Calculate yield using the relationship A260=1 corresponds to 40 µg/ml. Conversion factor for Spectramax=3.59 (i.e. multiply A260 by 3.59 when calculating yield).

8. In speed vac, dry down 10 µg per fluor-reversed pair.
9. Coupling Reactions: Resuspend 10 µg IVT product in 7 µl water (or water plus E1a) and divide into two tubes. One tube will be coupled with Cy3 and one with Cy5.

Preparation of 3× Sodium Bicarbonate Buffer:
Place the contents of one Carbonate-Bicarbonate Buffer capsule (Sigma, P/N C-3041) into a 50 ml Falcon tube.
Add 16.7 ml RNase free water and mix well.
Add 125 μl 37% HCl and mix.
pH should be 9–9.5.

Preparation of Cy-NHS Dyes:
Spin dye briefly before opening tube.
Add 10 μl anhydrous MSO to dye.
Mix by pipetting 20 times.
Set a pipettman at 3.5 μl.
Work quickly since the amino esters are unstable in aqueous environment.
Add 20 μl 3× sodium bicarbonate buffer to dye and mix well.
Add 3.5 μl dye to each tube of cRNA. Mix well.
Incubate in the dark for 1 hour.
Stop the reaction by adding 3.5 μl 4M HA (hydroxylamine)
Incubate 10 minutes.
10. Repeat RNeasy® clean-up as in Step 7, above, except elute in 70° C. nuclease-free water.
11. Measure yield and percent incorporation in a Costar UV plate. Calculate concentration of RNA using 1 $OD_{260}$=40 μg/ml RNA. Overall amplification yield is calculated by multiplying RNA concentration (μg/ml) by the sample volume (0.1 ml) and dividing by the amount of poly-$A^+$ RNA initially added to the reaction. Calculate concentration of Cy3-CTP using $\epsilon(552\ nm)=150$ (1/mMcm). Calculate concentration of Cy5-CTP using $\epsilon(650\ nm)=250$ (1/mMcm).

Generation of Gene Expression Profile Signatures:
Source mRNA from Jurkat and K562 cell lines was used to generate gene expression profile signatures by amplification and labeling using the Shannon method and using the random-primed RT-IVT method, followed by hybridization to DNA microarrays. Approximately 5 μg of Cy-labeled cRNA from each cell line was hybridized as fluor-reversed pairs to a DNA microarray pattern with probes tiled (overlapped) across all mRNA sequence for approximately 33 RefSeq test genes (LocusLink database, www.ncbi.nlm.nih.gov/locuslink/build.html) known to exhibit 3' amplification bias when amplified by the Shannon method. Analysis was performed either on a gene-by-gene basis or with all oligonucleotides at once. The first goal of the study was to determine whether the random-primed RT-IVT method produced a full-length cRNA. The second goal of the study was to determine whether the random-primed RT-IVT method has less of a 3' bias when compared with the Shannon method.

6.2. Results and Discussion

FIG. 1 compares the profiles obtained from single-gene analysis using the mRNA amplification method described in U.S. Pat. No. 6,132,997 (Shannon, issued Oct. 17, 2000) ("Shannon") and the random-primed RT-IVT method of the invention. The graphs plot signal intensity (mlavg) of oligonucleotides in a single gene (X-axis) as a function of the number of bp from the 5' end (Y-axis). The 3' bias of signal intensity seen when the Shannon method is used cannot be seen when the random-primed RT-IVT method is used, indicating that the random-primed RT-IVT method overcomes the 3' bias of the Shannon method.

FIG. 2 shows the intensity difference as a function of distance from the 3' end. The graph shows the intensity of all oligonucleotides as a function of distance from the 3' end. The graph plots mlavg (Shannon method)—mlavg (random-primed RT-IVT method) (X-axis) versus $\log_{10}$ of the number of bp from the 3' end (Y-axis). The intensity obtained with the Shannon method is greater than the intensity obtained with the random-primed RT-IVT method for probes less than 1000 bp from the 3' end of the message. The intensity obtained with the Shannon method is less than the intensity obtained with the random-primed RT-IVT method for probes greater than 1000 bp from the 3' end of the message.

At xdev threshold 2.5 (~Pvalue 1%), the following number of signatures were obtained (Table 2):

TABLE 2

| | Forward | | | Reverse | | |
|---|---|---|---|---|---|---|
| | total | bp < 1000 | bp > 1000 | total | bp < 1000 | bp > 1000 |
| random-primed RT-IVT | 2486 | 1488 | 998 | 2237 | 1367 | 870 |
| Shannon method | 2587 | 1927 | 660 | 1218 | 892 | 326 |
| # of probes | 7416 | 2965 | 4451 | 7413 | 2962 | 4451 |

FIGS. 3(A–C) shows the signature differences in the numbers and percentages of significant data points. The top graph (A) plots the number of probes (X-axis) versus the $[\log_{10}]$ (bp) (Y-axis). The middle graph (B) plots the number of signatures (X-axis) versus the $[\log_{10}]$ (bp) (Y-axis). The bottom graph (C) plots the fraction of signatures versus the $[\log_{10}]$ (bp) (Y-axis). As can be seen in the bottom graph, the random-primed RT-IVT method outcompetes the Shannon method for probes greater than 1000 bp from the 3' end. Note the black arrow at approximately 700 bp where random-primed RT-IVT method becomes better than the Shannon method. Stars: Shannon method. Circles: random-primed RT-IVT method.

FIGS. 4(A–C) shows the results obtained when the amplification methods of the invention were run using a primer comprising a T7 RNA polymerase promoter site and a poly-$dT_{18}$ sequence ("T7-$dT_{18}$"), in addition to using random T7-d $N_9$ and $dN_6$ primers. The top graph (A) plots the number of probes (X-axis) versus the $\log_{10}$ (bp) (Y-axis). The middle graph (B) plots the number of signatures (X-axis) versus the $\log_{10}$ (bp) (Y-axis). The bottom graph (C) plots the fraction of signatures versus the $\log_{10}$ (bp) (Y-axis). As can be seen in the bottom graph, the random-primed RT-IVT method helps improve the fraction of significant probes at bp<1000. Using both the T7-$dT_{18}$ and random T7-$dN_9$ primers for first strand cDNA synthesis improves the fraction of significant probes more efficiently than either the Shannon method or the method of the invention in which just the random T7-d $N_9$ primer is used. Stars: Shannon method. Circles: random-primed RT-IVT method.

These results indicate that the performance of random-primed RT-IVT is stable. The average yield obtained was 20 μg. The protocol produced little or no 3' bias and improved the ability to detect the 5' ends of mRNA. Linear amplification extents of 100-fold and labeling efficiencies of approximately 3% can be achieved using this method. When poly-dT and random dN primers, both of which comprise a T7 RNA polymerase promoter sequence, are used together to prime first strand cDNA synthesis, the fraction of significant probes is greater than that obtained with either the Shannon method or the method of the invention in which just a random T7-$dN_9$ primer is used.

The above results and discussion demonstrate that novel and improved methods of producing linearly amplified amounts of RNA from an initial RNA source are provided.

The methods of the invention provide an improvement over prior methods of producing linearly amplified RNA in that the protocol produces little or no 3' bias and improves the ability to detect the 5' ends of mRNA. Furthermore, linear amplification extents of at least 100-fold can be achieved using the subject methods. Finally, all of the benefits of linear amplification are achieved with the subject methods, such as the production of unbiased antisense RNA libraries from heterogeneous mRNA mixtures. As such, the subject methods represent a significant contribution to the art.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method for amplifying one or more single stranded nucleic acids, said method comprising:
   (a) producing double-stranded cDNA comprising contacting said one or more single stranded nucleic acids with:
      (i) a first set of oligonucleotides, each of said oligonucleotides in said first set comprising a promoter sequence operably linked to a random sequence at least 4 nucleotides in length from a set of random sequences of at least 4 nucleotides,
      (ii) a second set of oligonucleotides, each of said oligonucleotides in said second set comprising a random sequence of at least 4 nucleotides in length from a set of random sequences of at least 4 nucleotides, and
      (iii) one or more enzymes that alone or in combination catalyze the synthesis of double-stranded cDNA, under conditions suitable for the production of double-stranded cDNA; and
   (b) contacting the double-stranded cDNA produced in step (a) with a RNA polymerase that recognizes said promoter sequence and ribonucleotides under conditions suitable to effect transcription, thereby producing sense or antisense RNA copies corresponding to said one or more single stranded nucleic acids.

2. The method of claim 1, wherein the one or more single stranded nucleic acids are poly-$A^+$ RNA.

3. The method of claim 1, wherein the one or more enzymes is a reverse transcriptase.

4. The method of claim 3, wherein the reverse transcriptase is rendered incapable of RNA-dependent DNA polymerase activity during the transcription step.

5. The method of claim 4, wherein prior to step (b) said reverse transcriptase is inactivated.

6. The method of claim 5, wherein said reverse transcriptase is inactivated by heat.

7. The method of claim 1, wherein a single enzyme is employed for the synthesis of the double-stranded cDNA.

8. The method of claim 1, wherein the random sequences of the oligonucleotides in said first set of oligonucleotides are 6 to 9 nucleotides.

9. The method of claim 1, wherein the random sequences of the oligonucleotides in said second set of oligonucleotides are 6 to 9 nucleotides.

10. The method of claim 1, wherein the random sequences of the oligonucleotides in said first set of oligonucleotides are 9 nucleotides.

11. The method of claim 1, wherein the random sequences of the oligonucleotides in said second set of oligonucleotides are 6 nucleotides.

12. The method of claim 1, wherein the oligonucleotides in said second set of oligonucleotides do not comprise a promoter sequence.

13. The method of claim 1, wherein each oligonucleotide in said second set of oligonucleotides consists of a random sequence of at least 4 nucleotides in length from the set of random sequences of at least 4 nucleotides.

14. The method of claim 1, wherein step (a) further comprises contacting said one or more single-stranded nucleic acids with a third set of oligonucleotides each of said oligonucleotides in said third set comprising the promoter sequence operably linked to a polydT sequence of at least 5 nucleotides.

15. The method of claim 14, wherein said polydT sequence is 5 to 25 nucleotides.

16. The method of claim 15, wherein said polydT sequence is 18 nucleotides.

17. The method of claim 1, wherein the promoter sequence is a T7 RNA polymerase promoter sequence and the RNA polymerase is T7 RNA polymerase.

18. The method of claim 1, wherein the ribonucleotides comprise 5-(3-Aminoallyl)uridine 5'-triphosphate.

19. The method of claim 1, wherein the sense or antisense RNA copies are labeled with Cy-NHS.

20. The method of claim 19, wherein the Cy-NHS is Cy3-NHS or Cy5-NHS.

21. A method for amplifying one or more single stranded nucleic acids, said method comprising:
 (a) contacting said one or more single stranded nucleic acids with a first set of oligonucleotides, each of said oligonucleotides in said first set comprising a promoter sequence operably linked to a random sequence of at least 4 nucleotides in length from a set of random sequences of at least 4 nucleotides, and one or more enzymes that catalyze the synthesis of first strand cDNA, under conditions suitable for the production of first strand cDNA;
 (b) contacting the first strand cDNA produced in step (a) with a second set of oligonucleotides, each of said oligonucleotides in said second set comprising a random sequence of at least 4 nucleotides in length from a set of random sequences of at least 4 nucleotides and one or more enzymes that catalyze the synthesis of double-stranded cDNA, under conditions suitable for the production of double-stranded cDNA; and
 (c) contacting the double-stranded cDNA produced in step (b) with a RNA polymerase that recognizes said promoter sequence and ribonucleotides under conditions suitable to effect transcription, thereby producing sense or antisense RNA copies corresponding to said one or more single stranded nucleic acids.

* * * * *

UNITED STATES PATENT AND TRADEMARK OFFICE
CERTIFICATE OF CORRECTION

PATENT NO.        : 7,229,765 B2                                             Page 1 of 1
APPLICATION NO.   : 10/432176
DATED             : June 12, 2007
INVENTOR(S)       : M. Ziman et al.

It is certified that error appears in the above-identified patent and that said Letters Patent is hereby corrected as shown below:

On The Title Page,

Item (60)   Related U.S. Applic. Data   insert in appropriate order
--Related U.S. Application Data
Provisional application No. 60/253,641, filed on Nov. 28, 2000.--

Signed and Sealed this

Sixth Day of November, 2007

JON W. DUDAS
*Director of the United States Patent and Trademark Office*

SEQUENCE LISTING

```
<160> NUMBER OF SEQ ID NOS: 1

<210> SEQ ID NO 1
<211> LENGTH: 36
<212> TYPE: DNA
<213> ORGANISM: Artificial Sequence
<220> FEATURE:
<221> NAME/KEY: misc_feature
<222> LOCATION: 28..36
<223> OTHER INFORMATION: n = a, t, g, or c
<220> FEATURE:
<223> OTHER INFORMATION: Description of Artifical Sequence: Linker
      Sequence

<400> SEQUENCE: 1
aattaatacg actcactata gggagatnnn nnnnnn                               36
```